US011104651B2

(12) United States Patent
Lederkremer et al.

(10) Patent No.: US 11,104,651 B2
(45) Date of Patent: *Aug. 31, 2021

(54) PERK INHIBITORS AND USES THEREOF IN TREATING DISEASES ASSOCIATED WITH AGGREGATION-PRONE PROTEINS

(71) Applicant: Ramot at Tel-Aviv University Ltd., Tel-Aviv (IL)

(72) Inventors: Gerardo Zelmar Lederkremer, Shoham (IL); Julia Leitman, Petach-Tikva (IL); Hagit Eiger, Hadera (IL); Daniel Offen, Tel-Aviv (IL); Javier Ganz, Montevideo (UY); Moshe Portnoy, Ramat-HaSharon (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/920,710

(22) Filed: Jul. 5, 2020

(65) Prior Publication Data
US 2020/0331865 A1 Oct. 22, 2020

Related U.S. Application Data

(63) Continuation of application No. 16/066,697, filed as application No. PCT/IL2017/050655 on Jun. 13, 2017, now Pat. No. 10,723,706.

(60) Provisional application No. 62/349,170, filed on Jun. 13, 2016.

(51) Int. Cl.
*A61K 45/06* (2006.01)
*A61K 31/505* (2006.01)
*A61P 25/00* (2006.01)
*C07D 239/42* (2006.01)

(52) U.S. Cl.
CPC .......... *C07D 239/42* (2013.01); *A61K 31/505* (2013.01); *A61K 45/06* (2013.01); *A61P 25/00* (2018.01)

(58) Field of Classification Search
CPC ...... C07D 239/42; A61K 31/505; A61P 25/00
See application file for complete search history.

(56) References Cited

U.S. PATENT DOCUMENTS

2009/0163545 A1 6/2009 Goldfarb
2019/0010130 A1 1/2019 Lederkremer et al.

FOREIGN PATENT DOCUMENTS

| WO | WO 2007/074238 | * | 7/2007 |
| WO | WO 2011/119663 | | 9/2011 |
| WO | WO 2011/146748 | | 11/2011 |
| WO | WO 2017/216792 | | 12/2017 |

OTHER PUBLICATIONS

"Alzheimer's disease." CNN Health, Obtained Oct. 9, 2010, URL:http://www.cnn.com/2003/HEALTH/conditions/09/24/alzheimers.drug.ap/index.html.*
Antonio R. Damasio, Alzheimer's Disease and Related Dementias, Cecil Textbook of Medicine, 20th edition (1996), vol. 2, pp. 1992-1996.*
"Cataracts: Diagnosis & treatment," Mayo Clinic Staff, Jun. 23, 2018, Accessed May 13, 2019, Retrieved from <https://www.mayoclinic.org/diseases-conditions/cataracts/diagnosis-treatment/drc-20353795>.*
Machine translation of WO 2007/074238, accessed from espacenet, Translation received Aug. 17, 2020.*
International Search Report and the Written Opinion dated Sep. 19, 2017 From the International Searching Authority Re. Application No. PCT/IL2017/050655. (10 Pages).
Official Action dated May 16, 2019 From the US Patent and Trademark Office Re. U.S. Appl. No. 16/066,697. (15 pages).
Official Action dated Dec. 30, 2019 From the US Patent and Trademark Office Re. U.S. Appl. No. 16/066,697. (13 pages).
Supplementary European Search Report and the European Search Opinion dated Oct. 16, 2019 From the European Patent Office Re. Application No. 17812883.1. (8 Pages).
Atkins et al. "Characterization of a Novel PERK Kinase Inhibitor With Antitumor and Antiangiogenic Activity", Cancer Research, 73(6): 1993-2002, Mar. 15, 2013.

(Continued)

*Primary Examiner* — Alicia L Otton

(57) ABSTRACT

Compounds represented by Formula I are disclosed herein,

Formula I wherein R, Ra and $R_1$-$R_{14}$ are as defined herein. Further disclosed are uses and methods utilizing said compounds for use in inhibiting an activity of PERK, and in treating a disease or disorder associated with aggregation-prone proteins, a disease or disorder in which downregulating an unfolded protein response is beneficial, and/or Huntington's disease.

20 Claims, 7 Drawing Sheets

(56) References Cited

OTHER PUBLICATIONS

Axten et al. "Discovery of 7-Methyl-5-(1-{[3-(Trifluoromethyl)Phenyl]Acetyl}-2,3-Dihydro-1H-Indol-5-Yl)-7H-Pyrrolo[2,3-d]Pyrimidin-4-Amine (GSK2606414), A Potent and Selective First-in-Class Inhibitor of Protein Kinase R (PKR)-Like Endoplasmic Reticulum Kinase (PERK)", Journal of Medicinal Chemistry, 55(16): 7193-7207, Jul. 24, 2012.

Axten et al. "Discovery of GSK2656157: An Optimized PERK Inhibitor Selected for Preclinical Development", ACS Medicinal Chemistry Letters, 4(10): 964-968, Aug. 12, 2013.

Carnemolla et al. "Rrs1 is Involved in Endoplasmic Reticulum Stress Response in Huntington Disease", The Journal of Biological Chemistry, 284(27): 18167-18173, Published Online May 11, 2009.

CNN Health "FDA Mulls Drug to Slow Late-Stage Alzheimer's", Retrived from cnn.com, 2 pages, Sep. 24, 2003.

Colla et al. "Endoplasmic Reticulum Stress is Important for the Manifestations of Alpha-Synucleinopathy In Vivo", The Journal of Neuroscience, 32(10): 3306-3320, Mar. 7, 2012.

Costa-Mattioli et al. "E1F2Alpha Phosphorylation Bidirectionally Regulates the Switch From Short to Long-Term Synaptic Plasticity and Memory", Cell, 129(1): 195-206, Apr. 6, 2007.

Damasio "Alzheimer's Disease and Related Dementias", Cecil Textbook of Medicine, 20th Edition, 2: 1992-1996, 1996.

Das et al. "Preventing Proteostasis Diseases by Selective Inhibition of a Phosphatase Regulatory Subunit", Science, 348(6231): 239-243, Apr. 10, 2015.

Duennwald et al. "Impaired ERAD and ER Stress Are Early and Specific Events in Polyglutamine Toxicity", Genes & Development, 22(23): 3308-3319, Dec. 1, 2008.

Efrat "Genetically Engineered Pancreatic Beta-Cell Lines for Cell Therapy of Diabetes", Annals of the New York Academy of Sciences, 875(1):286-293, Jun. 18, 1999.

Guyenet et al. "A Simple Composite Phenotype Scoring System for Evaluating Mouse Models of Cerebellar Ataxia", Journal of Visualized Experiments, JoVE, 39: e1787-1-e1787-3, Published Online May 21, 2010.

Halliday et al. "Partial Restoration of Protein Synthesis Rates by the Small Molecule ISRIB Prevents Neurodegeneration Without Pancreatic Toxicity", Cell Death and Disease, 6(3): e1672-1-e1672-9, Published Online Mar. 5, 2015.

Krishnamoorthy et al. "Evidence of E1F2Alpha Phosphorylation-Independent Effects of GSK2656157, A Novel Catalytic Inhibitor of PERK With Clinical Implications", Cell Cycle, 13(5): 801-806, Jan. 8, 2014.

Leitman et al. "ER Stress-Induced E1F2-Alpha Phosphorylation Underlies Senstivity of Striatal Neurons to Pathogenic Huntingtin", PLOS ONE, 9(3): e90803-1-e90803-10, Mar. 3, 2014.

Leitman et al. "Soluble Forms of PolyQ-Expanded Huntingtin Rather Than Large Aggregates Cause Endoplasmic Reticulum Stress", Nature Communications, 4: 2753-1-2753-10, Nov. 12, 2013.

Li et al. "The Use of the R6 Transgenic Mouse Model of Huntington's Disease in Attempts to Develop Novel Therapeutic Strategies", NeuroRx, 2(3): 447-464, Jul. 2005.

Ma et al. "Suppression of E1F2Alpha Kinases Alleviates AD-Related Synaptic Plasticity and Spatial Memory Deficits", Nature Neuroscience, 16(9): 1299-1305, Sep. 2013.

Mangiarini et al. "Exon 1 of the HD Gene With an Expanded CAG Repeat is Sufficient to Cause a Progressive Neurological Phenotype in Transgenic Mice", Cell, 87(3): 493-506, Nov. 1, 1996.

Mayo Clinic "Cataracts: Diagnosis & Treatment", Retrieved from mayoclinic.org, 4 pages, Jun. 23, 2018.

Moreno et al. "Oral Treatment Targeting the Unfolded Protein Response Prevents Neurodegeneration and Clinical Disease in Prion-Infected Mice", Science Translational Medicine, 5(206): 206ra138-1-206ra138-10, Oct. 9, 2013.

Moreno et al. "Sustained Translational Repression by E1F2Alpha-P Mediates Prion Neurodegeneration", Nature, 485(7399): 507-511, May 24, 2012.

Radford et al. "PERK Inhibition Prevents Tau-Mediated Neurodegeneration in a Mouse Model of Frontotemporal Dementia", Acta Nemopathologica, 130(5): 633-642, Published Online Oct. 8, 2015.

Reijonen et al. "Inhibition of Endoplasmic Reticulum Stress Counteracts Neuronal Cell Death and Protein Aggregation Cuased by N-Terminal Mutant Huntingtin Proteins", Experimental Cell Research, 314: 950-960, Available Online Jan. 14, 2008.

Rojas-Rivera et al. "When PERK inhibitors Turn to Be New Potent RIPK1 Inhibitors: Critical Issues on the Specificity and Use of GSK2606414 and GSK2656157", Cell Death and Differentiation, 24(6): 1100-1110, Published Online Apr. 28, 2017.

Sidrauski et al. "Pharmacological Brake-Release of mRNA Translation Enhances Cognitive Memory", eLife, 2: e00498-1-e00498-22, May 28, 2013.

Tsaytler et al. "Selective Inhibition of a Regulatory Subunit of Protein Phosphatase 1 Restores Proteostasis", Science, 332(6025): 91-94, Apr. 1, 2011.

Vieira et al. "Guanabenz Treatment Accelerates Disease in a Mutant SOD1 Mouse Model of ALS", PLoS ONE, 10(8): e0135570-1-e0135570-15, Aug. 19, 2015.

Wang et al. "Structural Determinants of PERK Inhibitor Potency and Selectivity", Chemical Biology & Drug Design, XP055078522, 76(6): 480-495, Dec. 1, 2010. Compound A4, Table 1, p. 483.

* cited by examiner

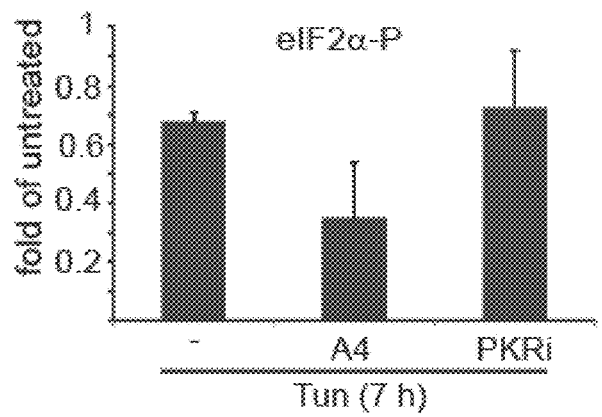
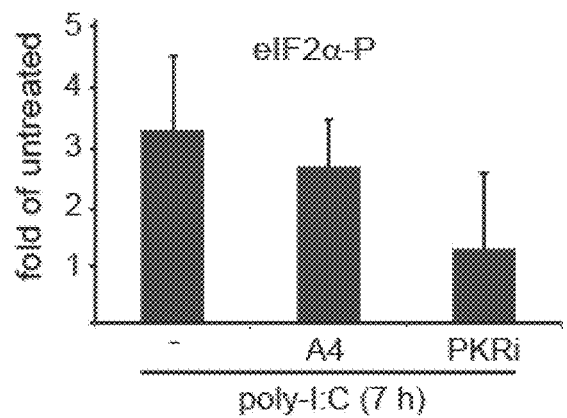
FIG. 2A
FIG. 2B
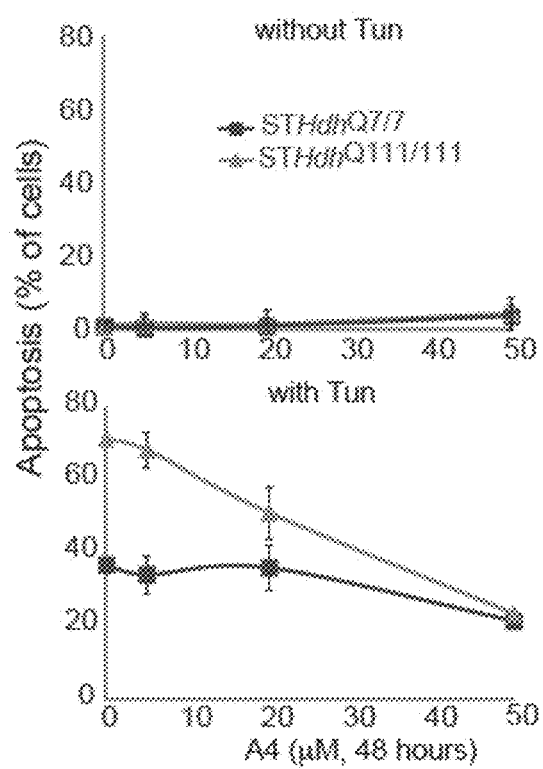
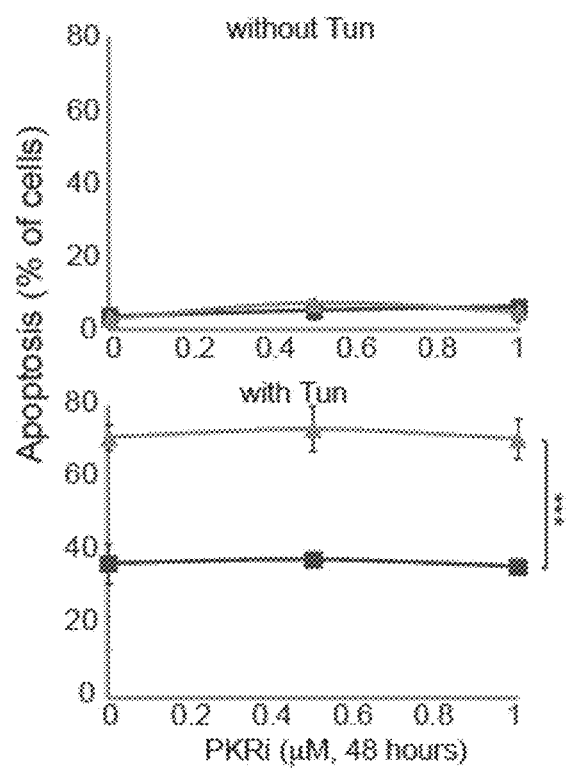
FIG. 2C
FIG. 2D

PERK INHIBITORS AND USES THEREOF IN TREATING DISEASES ASSOCIATED WITH AGGREGATION-PRONE PROTEINS

RELATED APPLICATIONS

This application is a continuation of U.S. patent application Ser. No. 16/066,697 filed on Jun. 28, 2018, which is a National Phase of PCT Patent Application No. PCT/IL2017/050,655 having International Filing Date of Jun. 13, 2017, which claims the benefit of priority under 35 USC § 119(e) of U.S. Provisional Patent Application No. 62/349,170 filed on Jun. 13, 2016. The contents of the above applications are all incorporated by reference as if fully set forth herein in their entirety.

FIELD AND BACKGROUND OF THE INVENTION

The present invention, in some embodiments thereof, relates to therapy, and more particularly, but not exclusively, to compounds which inhibit pancreatic endoplasmic reticulum kinase (PERK) activity and which are usable in treating diseases associated with aggregation-prone proteins, such as Huntington's disease.

Protein aggregation is a biological phenomenon in which misfolded proteins form, either intracellularly or extracellularly, aggregates which are often toxic. Aggregation-prone proteins produce cellular stress, toxicity and death and are the cause of many of the neurodegenerative diseases, including, for example, ALS, Alzheimer's, Parkinson's and prion disease.

Proteins fold into their native conformation and undergo a series of post-translational modifications in the endoplasmic reticulum (ER) as part of the normal process of cellular homeostasis. Disruption of cellular protein folding results in ER stress. Cells respond to ER stress by activation of the unfolded protein response (UPR) pathways to survive the stress.

Pancreatic endoplasmic reticulum kinase (PERK), one of the three identified UPR transducers, is a kinase that phosphorylates a single known substrate eIF2α, leading to lower levels of translation initiation, which in turn globally reduces the load of newly synthesized proteins in the ER. Reduction in the overall protein-folding load is an effective response to reduce ER stress. In addition, PERK-mediated eIF2α phosphorylation also induces transcriptional activation to improve protein-folding capacity, thereby further promoting cell survival in stressed cells. Among the group of three prominent UPR transducers that includes also XBP1 and ATF6, PERK may have a broader range of cellular effects than other transducers, perhaps because of its unique role in regulating the general translation rate through the phosphorylation of eIF2α. Indeed, eIF2α phosphorylation appears to account for the entire range of the protective effects of PERK under ER stress. See, for example, Wang et al. [*Chem Biol Drug Des* 2010, 76: 480-495], and references cited therein.

Huntington's disease (HD) is a neurodegenerative disease, which initially affects medium spiny neurons in the brain striatum, and only later regions of the brain cortex.

HD is a progressive, fatal genetic disorder affecting cognition and movement. HD is characterized by high sensitivity of striatal cells, the reasons of which are unknown, though mechanisms have been proposed involving proteins with enhanced expression in these cells. A hallmark of Huntington's disease is the pronounced sensitivity of striatal neurons to polyglutamine-expanded huntingtin expression.

HD arises from mutant forms of the huntingtin (Htt) protein with expanded polyglutamine (polyQ) tracts (>35 amino acids). This mutation causes Htt aggregation, which interferes with normal cell metabolism, leading to cytotoxicity. One of the effects of the expression of mutant Htt is the activation of the unfolded protein response (UPR) [Carnemolla et al., *J Biol Chem* 2009, 284: 18167-18173; Duennwald & Lindquist, *Genes Dev* 2008, 22: 3308-3319; Leitman et al., *Nat Commun* 2013, 4:2753; Reijonen et al., *Exp Cell Res* 2008, 314: 950-960].

Some of the present inventors have previously determined that in cells expressing mutant Huntington, the causative agent of Huntington's disease (HD), there is a strong induction of endoplasmic reticulum (ER) stress, especially in striatal cells, the cells that first degenerate in HD patients; and have showed that huntingtin toxicity was reduced by inhibiting PERK [Leitman et al., *PLoS One* 2014, 9(3): e90803; Leitman et al., *Nat Commun* 2013, 4:2753].

Small molecules inhibitors of PERK, designed mainly for treating cancer, but also in the context of neurodegenerative diseases such as prion disease, have been described, for example, in Wang et al. [*Chem Biol Drug Des* 2010, 76: 480-495]; Axten et al. [*J Med Chem* 2012, 55: 7193-7207]; Axten et al. [*ACS Med Chem Lett* 2013, 4:964-968]; Moreno et al. [*Sci Transl Med* 2013, 5(206):206ra138]; Radford et al. [*Acta Neuropathol* 2015, 130:633-642]; and International Patent Application Publications WO 2011/119663 and WO 2011/146748. These include, for example, the recently developed GSK2606414 and GSK2656157, and a molecule denoted A4, the structures of which are presented herein below.

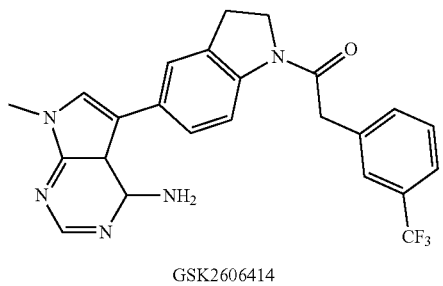

GSK2606414

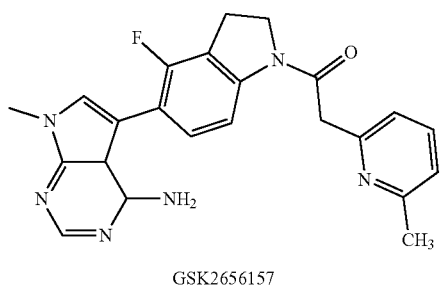

GSK2656157

-continued

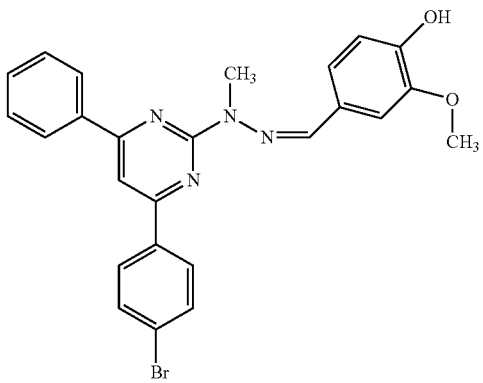

A4

GSK2606414 and GSK2656157 have been reported to be potent inhibitors of RIPK1, which renders their use as PERK inhibitors difficult to interpret [Rojas-Rivera et al., *Cell Death Differ* 2017, 24:1100-1110].

Additional background art includes Atkins et al. [*Cancer Res* 2013, 73:1993-2002]; Colla et al. [*J Neurosci* 2012, 32:3306-3320]; Costa-Mattioli et al. [*Cell* 2007, 129:195-206]; Das et al. [*Science* 2015, 348:239-242]; Efrat [*Ann NY Acad Sci* 1999, 875:286-293]; Guyenet et al. [*J Vis Exp* 2010, (39):1787]; Halliday et al. [*Cell Death Dis* 2015, 6:e1672]; Krishnamoorthy et al. [*Cell Cycle* 2014, 13:801-806]; Li et al. [*NeuroRx* 2005, 2:447-464]; Ma et al. [*Nat Neurosci* 2013, 16:1299-1305]; Mangiarini et al. [*Cell* 1996, 87:493-506]; Moreno et al. [*Nature* 2012, 485:507-511]; Sidrauski et al. [*Elife* 2013, 2:e00498]; Tsaytler et al. [*Science* 2011, 332:91-94]; Vieira et al. [*PloS One* 2015; 10(8): e0135570]; and U.S. Patent Application Publication No. 2009-0163545.

SUMMARY OF THE INVENTION

According to an aspect of some embodiments of the invention, there is provided a compound represented by Formula I*:

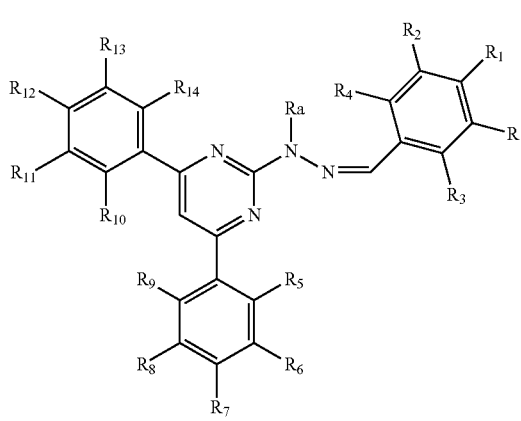

Formula I* wherein:

$R_2$ is H;

$R_1$ is OH;

R is OH or OR';

R' is selected from the group consisting of alkyl, cycloalkyl, heteroalicyclic, aryl and heteroaryl;

$R_3$ and $R_4$ are each hydrogen;

Ra is alkyl;

$R_5$-$R_{14}$ are each independently selected from the group consisting of hydrogen, alkyl, alkenyl, alkynyl, cycloalkyl, aryl, heteroaryl, heteroalicyclic, halo, hydroxy, alkoxy, sulfonate, sulfoxide, thiosulfate, sulfate, sulfite, thiosulfite, phosphonate, thiohydroxy, thioalkoxy, cyano, nitro, azo, sulfonamide, carbonyl, thiocarbonyl, C-carboxylate, O-carboxylate, N-thiocarbamate, O-thiocarbamate, acyl halide, azide, urea, thiourea, N-carbamate, O-carbamate, C-amide, N-amide, hydrazine and hydrazide, for use in treating Huntington's disease.

According to an aspect of some embodiments of the invention, there is provided a compound represented by Formula I:

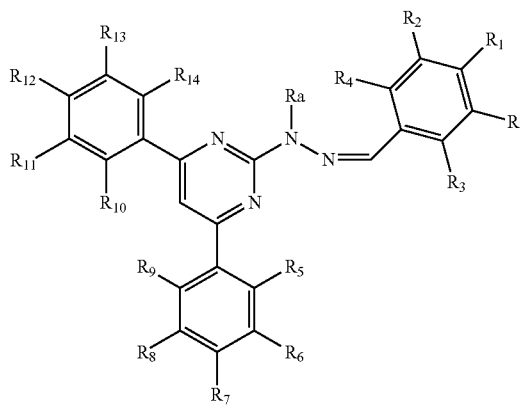

Formula I wherein:

$R_2$ is H;

$R_1$ is OH;

R is OH or OR';

R' is selected from the group consisting of alkyl, cycloalkyl, heteroalicyclic, aryl and heteroaryl;

$R_3$ and $R_4$ are each hydrogen;

Ra is alkyl;

$R_5$-$R_{14}$ are each independently selected from the group consisting of hydrogen, alkyl, alkenyl, alkynyl, cycloalkyl, aryl, heteroaryl, heteroalicyclic, halo, hydroxy, alkoxy, sulfonate, sulfoxide, thiosulfate, sulfate, sulfite, thiosulfite, phosphonate, thiohydroxy, thioalkoxy, cyano, nitro, azo, sulfonamide, carbonyl, thiocarbonyl, C-carboxylate, O-carboxylate, N-thiocarbamate, O-thiocarbamate, acyl halide, azide, urea, thiourea, N-carbamate, O-carbamate, C-amide, N-amide, hydrazine and hydrazide, with the proviso that when R is OR', and R' is methyl, $R_7$ and $R_{12}$ are each other than bromo, for use in inhibiting an activity of PERK.

According to an aspect of some embodiments of the invention, there is provided a compound represented by Formula I:

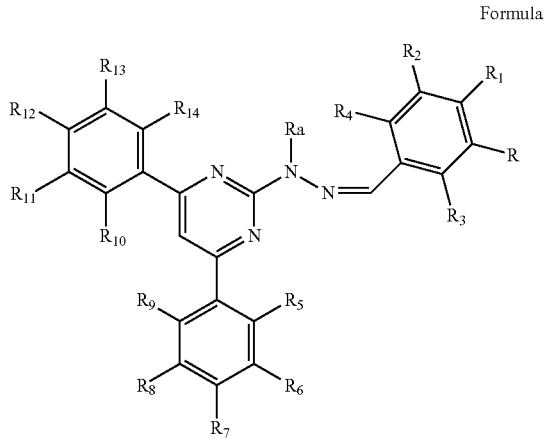

Formula I wherein:
$R_2$ is H;
$R_1$ is OH;
R is OH or OR';
R' is selected from the group consisting of alkyl, cycloalkyl, heteroalicyclic, aryl and heteroaryl;
$R_3$ and $R_4$ are each hydrogen;
Ra is alkyl;
$R_5$-$R_{14}$ are each independently selected from the group consisting of hydrogen, alkyl, alkenyl, alkynyl, cycloalkyl, aryl, heteroaryl, heteroalicyclic, halo, hydroxy, alkoxy, sulfonate, sulfoxide, thiosulfate, sulfate, sulfite, thiosulfite, phosphonate, thiohydroxy, thioalkoxy, cyano, nitro, azo, sulfonamide, carbonyl, thiocarbonyl, C-carboxylate, O-carboxylate, N-thiocarbamate, O-thiocarbamate, acyl halide, azide, urea, thiourea, N-carbamate, O-carbamate, C-amide, N-amide, hydrazine and hydrazide,
with the proviso that when R is OR', and R' is methyl, $R_7$ and $R_{12}$ are each other than bromo,
for use in treating a disease or disorder associated with aggregation-prone proteins.

According to an aspect of some embodiments of the invention, there is provided a compound represented by Formula I:

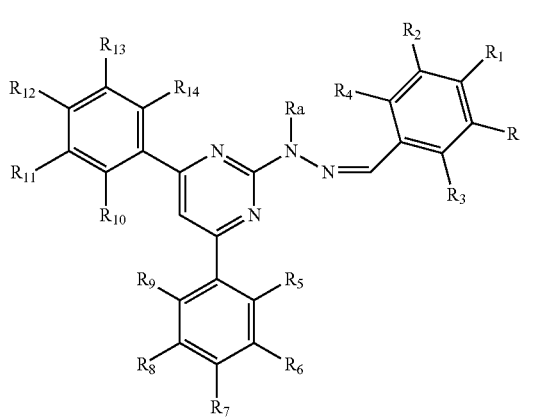

Formula I wherein:
$R_2$ is H;
$R_1$ is OH;
R is OH or OR';
R' is selected from the group consisting of alkyl, cycloalkyl, heteroalicyclic, aryl and heteroaryl;
$R_3$ and $R_4$ are each hydrogen;
Ra is alkyl;
$R_5$-$R_{14}$ are each independently selected from the group consisting of hydrogen, alkyl, alkenyl, alkynyl, cycloalkyl, aryl, heteroaryl, heteroalicyclic, halo, hydroxy, alkoxy, sulfonate, sulfoxide, thiosulfate, sulfate, sulfite, thiosulfite, phosphonate, thiohydroxy, thioalkoxy, cyano, nitro, azo, sulfonamide, carbonyl, thiocarbonyl, C-carboxylate, O-carboxylate, N-thiocarbamate, O-thiocarbamate, acyl halide, azide, urea, thiourea, N-carbamate, O-carbamate, C-amide, N-amide, hydrazine and hydrazide,
with the proviso that when R is OR', and R' is methyl, $R_7$ and $R_{12}$ are each other than bromo,
for use in treating a disease or disorder in which down-regulating an unfolded protein response is beneficial.

According to some embodiments of any of the embodiments of the invention, the compound is for use in treating a disease or disorder in which PERK inhibition is beneficial.

According to some embodiments of any of the embodiments of the invention, $R_7$ and $R_{12}$ are each other than bromo.

According to some embodiments of any of the embodiments of the invention, when R is OR', and R' is methyl, $R_7$ and $R_{12}$ are each other than bromo.

According to some embodiments of any of the embodiments of the invention, $R_7$ and $R_{12}$ are each hydrogen.

According to some embodiments of any of the embodiments of the invention, Ra is methyl.

According to some embodiments of any of the embodiments of the invention, $R_5$-$R_{14}$ are each hydrogen.

According to some embodiments of any of the embodiments of the invention, $R_3$-$R_{14}$ are each hydrogen.

According to some embodiments of any of the embodiments of the invention, R is OR'.

According to some embodiments of any of the embodiments of the invention, R' is methyl.

According to some embodiments of any of the embodiments of the invention, the compound is Compound 1:

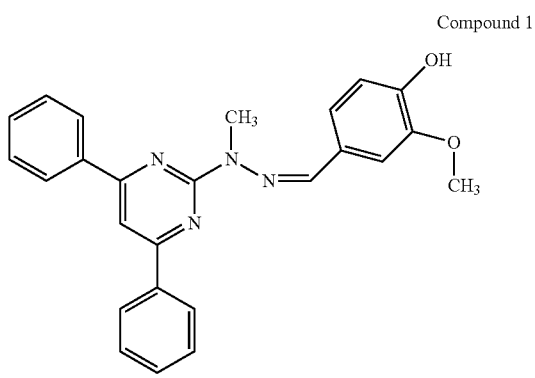 [SMILES: COc1cc(/C=N\N(C)c2nc(-c3ccccc3)cc(-c3ccccc3)n2)ccc1O]

Compound 1

According to some embodiments of any of the embodiments of the invention, R is OH.

According to some embodiments of any of the embodiments of the invention, the compound is Compound 3:

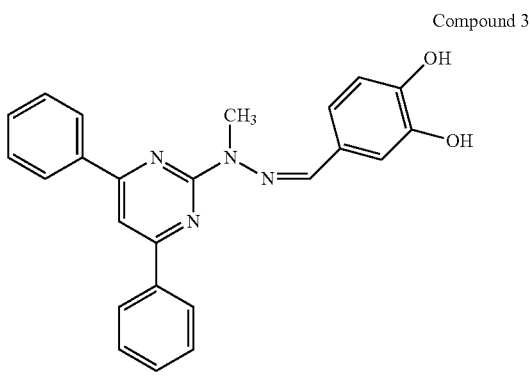 [SMILES: CN(/N=C\c1ccc(O)c(O)c1)c1nc(-c2ccccc2)cc(-c2ccccc2)n1]

Compound 3

According to an aspect of some embodiments of the invention, there is provided the compound:

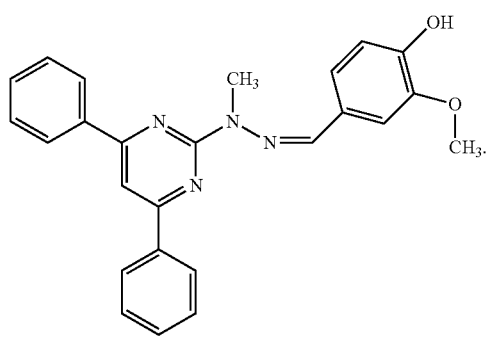 [SMILES: COc1cc(/C=N\N(C)c2nc(-c3ccccc3)cc(-c3ccccc3)n2)ccc1O]

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-2D present bar graphs (FIGS. 2A-2B) and comparative plots (FIGS. 2C-2D) showing the regulation of phosphorylated eIF2α levels by inhibition of its phosphorylation and rescue of STHdhQ111/111 cells. FIG. 2A is a bar graph showing that ER stress-mediated eIF2α phosphorylation in STHdh$^{Q7/7}$ cells treated with Tun (5 μg/ml for 48 hours) is inhibited by A4 (50 μM) and not by PKRi (1 μM). FIG. 2B is a bar graph showing that PKR activity (induced with poly-I:C) was inhibited by PKRi and not A4. FIGS. 2C-2D present comparative plots showing that A4 rescued STHdhQ111/111 cells from UPR-induced cell death (Tun for 48 hours, FIG. 2C), whereas PKRi had no effect (FIG. 2D). Apoptosis was measured by cell cycle progression using propidium iodide (PI), considering the fraction beneath G0/G1.

FIG. 3A shows comparative data obtained for A4, MPGL1 (Compound 1) and MK-28 (Compound 3) in rescuing STHdhQ111/111 cells from UPR-induced cell death (Tun for 48 hours), as described for FIGS. 2C-2D, whereby in FIG. 3B comparative data is shown for cells incubated for 48 hours in DMEM without serum and without Tun. In this assay, A4 shows a minimal effect, compared to the strong rescue effect of MK-28.

N=13 TG, 13 TG+MK28, 16 WT, 15 WT+MK28, 15 None; *p<0.05 Anova Newman-Keuls post hoc.

Figure 8:
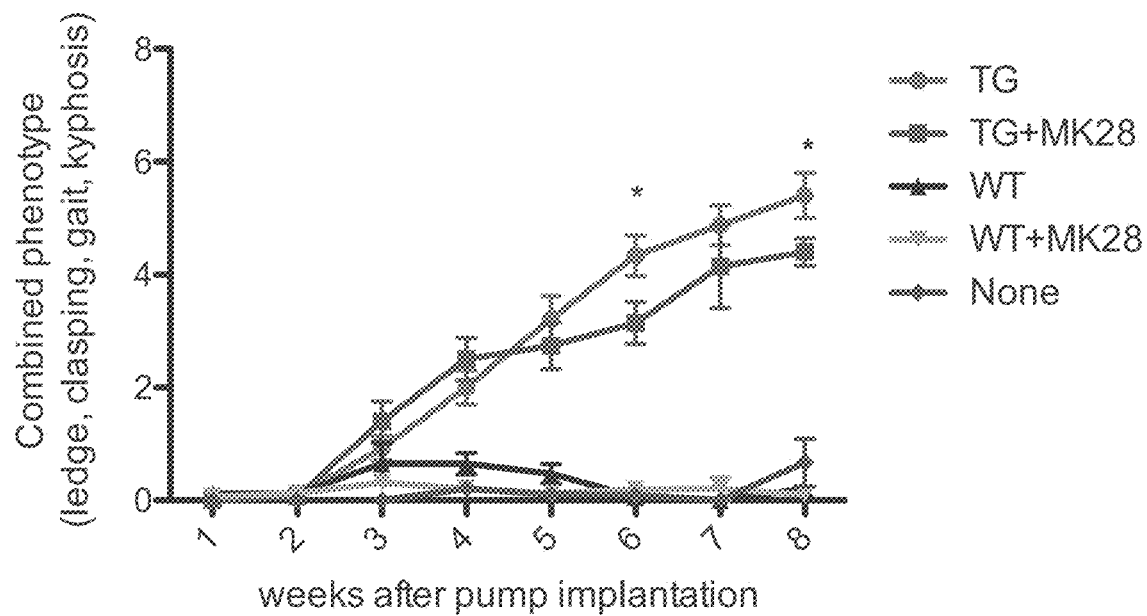
FIG. 8 presents comparative plots presenting data obtained in a combined motor function test, showing a significant improvement upon treatment of R6/2 mice with MK-28. Animals were treated as described in FIG. 6. Combined phenotype was measured, including ledge, clasping, gait and kyphosis. TG mice showed a strong deficiency, which was significantly reduced with MK-28 treatment.
Figure 9:
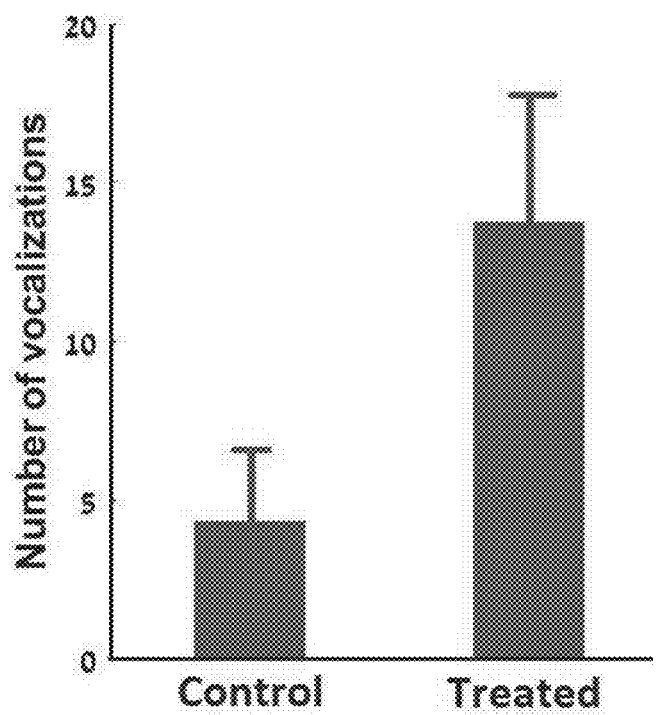

FIG. 9 is a bar graph demonstrating that ultrasonic vocalizations of R6/2 mice are improved by treatment with MK-28. Mice were treated as described in FIGS. 7 and 8. Transgenic mice receiving (MK-28 TG+) or vehicle (TG) were analyzed for vocalization as number of syllables in 5 minutes intervals. (n=3-4, p=0.059).

Figure 10:
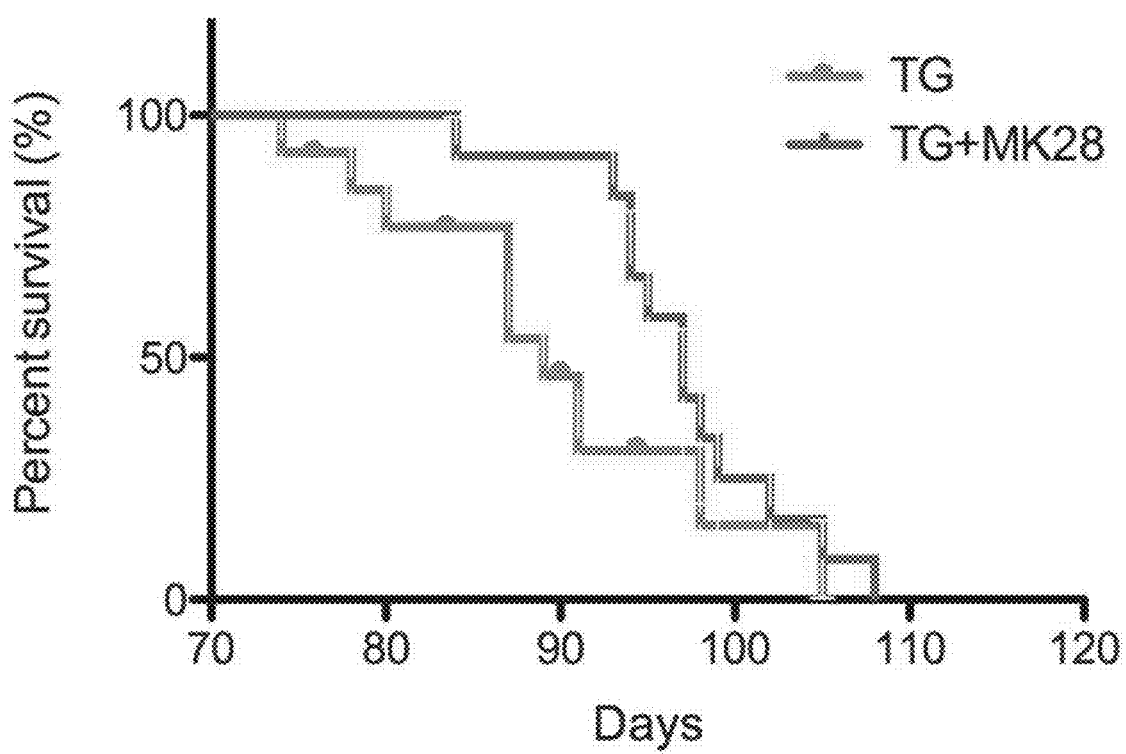

FIG. 10 presents comparative plots demonstrating that survival of R6/2 mice is significantly increased upon treatment with MK-28. Animals were treated as described in FIGS. 7-9. Transgenic mice receiving MK-28 (blue) or vehicle (red) were analyzed for mice survival (n=13/group). Gehan-Breslow-Wilcoxon Test for comparisons of Kaplan-Meier survival curves indicated a significant increase in the survival of MK-28 treated mice compared to untreated littermates (median survival 97 and 89 days, respectively, p=0.0469). Ratio 1.887, 95% CI of ratio 0.7726 to 4.611.

DESCRIPTION OF SPECIFIC EMBODIMENTS OF THE INVENTION

The present invention, in some embodiments thereof, relates to therapy and, more particularly, but not exclusively, to novel compounds which are capable of inhibiting pancreatic endoplasmic reticulum kinase (PERK) activity and which are usable in treating diseases associated with aggregation-prone proteins, such as Huntington's disease.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Figure 1:
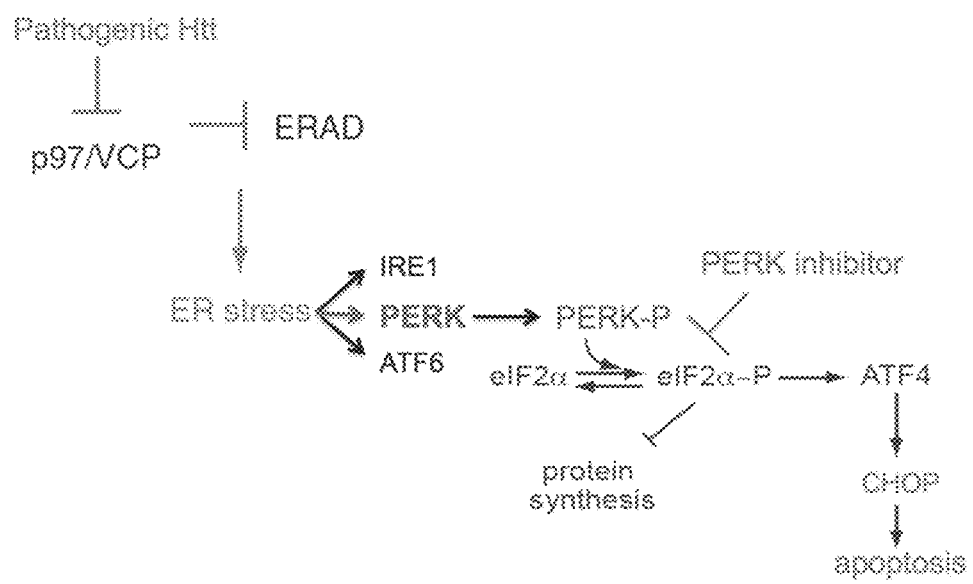
FIG. 1 (Background Art) is a scheme depicting the regulation of phosphorylated eIF2α levels by inhibition of its phosphorylation, showing Htt cytotoxicity in striatal neurons as concluded from studies described in Leitman et al. [*PLoS One* 2014, 9(3):e90803]. Cytotoxic steps are in red and PERK and its activated form PERK-P are highlighted in blue. The site of action of a PERK inhibitor is shown.

Phosphorylation of eIF2α by PERK in response to ER stress has two opposing effects, protective in the short-term and cytotoxic in the long-term. Therefore, both, the long-term inhibition of protein synthesis by phosphorylation of eIF2α and the total lack of its phosphorylation and consequent absence of transient translation inhibition, can be cytotoxic, as shown, for example, in Background Art FIG. 1.

Consequently, in principle, two opposite strategies for therapy could be used in diseases that cause ER stress; partial inhibition and partial enhancement of eIF2α phosphorylation. The latter approach is controversial, as it has been shown that inhibition of GADD34 (PPP1R15A, the UPR-induced regulatory subunit of the phosphatase that dephosphorylates eIF2α) was neuroprotective in mouse models of prion disease, Parkinson's disease and ALS [Colla et al., *J Neurosci* 2012, 32:3306-3320; Das et al., *Science* 2015, 348:239-242; Tsaytler et al., *Science* 2011, 332:91-94]; yet it was shown as detrimental in prion disease and ALS models in other studies [Moreno et al., *Nature* 2012, 485:507-511; Vieira et al., *PloS One* 2015; 10(8):e0135570].

Given the benefits of partial PERK inhibition, but the possible toxicity of total inhibition in some tissues, the protective activity of inhibitors can be measured by the rescue of cells from apoptosis.

The dephosphorylated state of eIF2α has been shown to regulate memory and long-term potentiation, possibly by maintaining high translation rates [Costa-Mattioli et al., *Cell* 2007, 129:195-206; Sidrauski et al., *Elife* 2013, 2:e00498]. Therefore, ER stress and the consequent increase in eIF2α-P levels in neurodegenerative diseases could be directly linked to cognitive impairment.

The present inventors have conceived that small molecule inhibitors of PERK can reduce the level of eIF2α phosphorylation in response to pathogenic huntingtin.

A4 is a small molecule reported to inhibit PERK activity in vitro [Wang et al., *Chem Biol Drug Des* 2010, 76:480-495]. The present inventors have designed and successfully prepared structural analogs of A4 and have found that these compounds exhibit a much stronger effect than A4 in reducing huntingtin-mediated cytotoxicity in striatal cells in culture.

While reducing the present invention to practice, the inventors have demonstrated that PERK inhibitors exhibit exceptional activity both in striatal neurons in culture and in the R6/2 HD model mice, as shown in FIGS. 3A-10. Given the harsh phenotypic consequences of mutant Htt expression in this mouse model, the improvement seen in a variety of motor and behavioral parameters, and the increase in survival by the herein disclosed treatment, are remarkable.

The most active compound, MK-28 (Compound 3), was further tested in HD model mice and significantly ameliorated the symptoms of disease in these mice, prolonging their lifespan.

The data presented herein demonstrates the potential efficacy of PERK inhibitors, and of the novel PERK inhibitors disclosed herein in particular, in HD therapy. Given the similar ER stress pathways involved, the novel PERK inhibitors disclosed herein are also candidates for therapy of many other neurodegenerative and other diseases associated with aggregation-prone proteins.

According to an aspect of some embodiments of the present invention, there is provided a compound having the general Formula I:

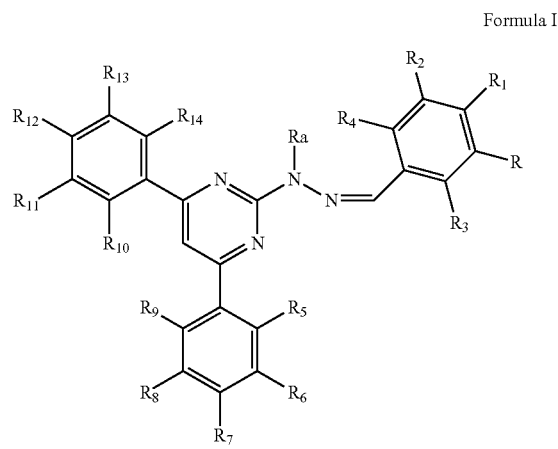

Formula I for use in inhibiting an activity of PERK and/or for use in treating a disease or disorder as described herein, wherein Ra, R and $R_{1-14}$ are as defined hereinafter in any of the respective embodiments and any combination thereof.

Compounds:

The compounds described in some embodiments of any of the aspects of the present embodiments are collectively represented by Formula I:

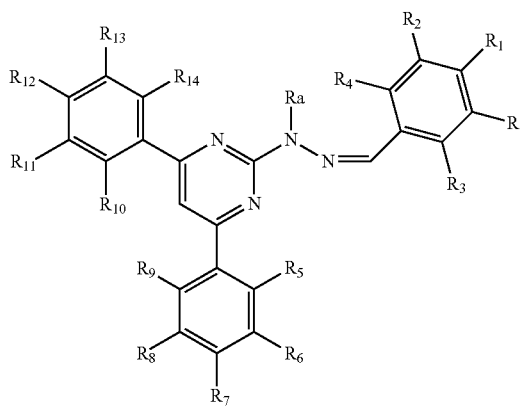

Formula I wherein:

$R_1$, $R_2$ and R are each independently H, OH or OR', with R' being alkyl, cycloalkyl, heteroalicyclic, aryl or heteroaryl, as defined herein;

$R_3$ and $R_4$ are each independently hydrogen, substituted or unsubstituted alkyl (e.g., unsubstituted alkyl, hydroxyalkyl or trihaloalkyl), substituted or unsubstituted alkenyl, substituted or unsubstituted alkynyl, substituted or unsubstituted cycloalkyl, substituted or unsubstituted aryl, substituted or unsubstituted heteroaryl, substituted or unsubstituted heteroalicyclic, halo, hydroxy, alkoxy, sulfonate, sulfoxide, thiosulfate, sulfate, sulfite, thiosulfite, phosphonate, thiohydroxy, thioalkoxy, cyano, nitro, azo, sulfonamide, carbonyl, thiocarbonyl, C-carboxylate, O-carboxylate, N-thiocarbamate, O-thiocarbamate, acyl halide, azide, urea, thiourea, N-carbamate, O-carbamate, C-amide, N-amide, hydrazine or hydrazide, as these terms are defined hereinafter;

Ra is H or a substituted or unsubstituted alkyl;

$R_5$-$R_{14}$ are each independently hydrogen, substituted or unsubstituted alkyl (e.g., unsubstituted alkyl, hydroxyalkyl or trihaloalkyl), substituted or unsubstituted alkenyl, substituted or unsubstituted alkynyl, substituted or unsubstituted cycloalkyl, substituted or unsubstituted aryl, substituted or unsubstituted heteroaryl, substituted or unsubstituted heteroalicyclic, halo, hydroxy, alkoxy, sulfonate, sulfoxide, thiosulfate, sulfate, sulfite, thiosulfite, phosphonate, thiohydroxy, thioalkoxy, cyano, nitro, azo, sulfonamide, carbonyl, thiocarbonyl, C-carboxylate, O-carboxylate, N-thiocarbamate, O-thiocarbamate, acyl halide, azide, urea, thiourea, N-carbamate, O-carbamate, C-amide, N-amide, hydrazine or hydrazide (optionally hydrogen, alkyl or halo), as these terms are defined hereinafter.

According to the present embodiments, Formula I can otherwise be presented as follows:

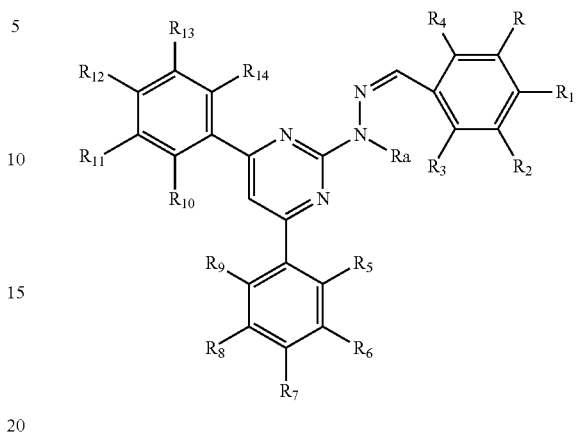

In some embodiments of any of the embodiments described herein, R' is alkyl. In some embodiments, the alkyl is unsubstituted. In some embodiments, R' is $C_{1-4}$-alkyl, optionally unsubstituted $C_{1-4}$-alkyl. In exemplary embodiments, R' is methyl.

In some embodiments of any of the embodiments described herein, $R_1$ is OH.

In some embodiments of any of the embodiments described herein, $R_2$ is H or OR'. In some embodiments, $R_2$ is H. In some embodiments, R' is methyl.

In some embodiments of any of the embodiments described herein, $R_1$ is OH and $R_2$ is H or OR'. In some such embodiments, R' is methyl.

In some embodiments of any of the embodiments described herein, $R_1$ is OH and $R_2$ is H.

In some embodiments of any of the embodiments described herein, R is OH or OR'. In some embodiments, R is OH or OR' and $R_1$ is OH.

In some embodiments of any of the embodiments described herein, R is OH or OR' and $R_2$ is H or OR'. In some such embodiments, $R_2$ is H. In some such embodiments, R' is methyl.

In some embodiments of any of the embodiments described herein, R is OH or OR', $R_1$ is OH and $R_2$ is H or OR'. In some such embodiments, R' is methyl.

In some embodiments of any of the embodiments described herein, R is OH or OR', $R_1$ is OH and $R_2$ is H. In some such embodiments, R' is methyl.

In some embodiments of any of the embodiments described herein, $R_3$ and $R_4$ are each hydrogen or alkyl. In some embodiments, $R_3$ and $R_4$ are each hydrogen.

In some embodiments of any of the embodiments described herein, $R_7$ is other than bromo. In some such embodiments, $R_7$ is other than halo.

It is to be understood that limitations regarding any of the variables $R_5$-$R_{14}$ apply also to other variables which are at equivalent positions in Formula I. For example, as $R_7$ and $R_{12}$ are at equivalent positions in Formula I, the limitation "$R_7$ is other than bromo" (or halo) is to be understood as meaning that "neither $R_7$ nor $R_{12}$ is bromo" (or halo), and vice versa; and "$R_7$ is hydrogen" is to be understood as meaning that "$R_7$ and $R_{12}$ are each hydrogen", and vice versa.

Without being bound by any particular theory, it is believed that the enhanced activity of the exemplary compound Compound 1 (MPGL1)—relative to the compound A4—may be attributed to the elimination of the bulky bromo substituent of A4, e.g., by reducing its steric hindrance.

In some embodiments of any of the embodiments described herein, when R is OR', R' is methyl, Ra is methyl, and $R_3$-$R_6$ and $R_8$-$R_{14}$ are each hydrogen, neither $R_7$ nor $R_{12}$ is bromo. In some such embodiments, neither $R_7$ nor $R_{12}$ is halo.

In some embodiments of any of the embodiments described herein, when R is OR', and R' is methyl, neither $R_7$ nor $R_{12}$ is bromo. In some such embodiments, neither $R_7$ nor $R_{12}$ is halo.

In some embodiments of any of the embodiments described herein, when R is OR', neither $R_7$ nor $R_{12}$ is bromo. In some such embodiments, neither $R_7$ nor $R_{12}$ is halo.

In some of any of the embodiments described herein wherein $R_7$ (and/or $R_{12}$) is other than bromo, $R_7$ (and/or $R_{12}$) is a halo other than bromo, for example, chloro or fluoro (e.g., halogen substituents less bulky than bromo).

In some embodiments of any of the embodiments described herein, $R_7$ is hydrogen. In some embodiments, R is OR', and $R_7$ is hydrogen. In some embodiments, R is OR', and $R_5$-$R_{14}$ are each hydrogen.

In some embodiments of any of the embodiments described herein, $R_5$-$R_{14}$ are each hydrogen. In some embodiments of any of the embodiments described herein, $R_3$-$R_{14}$ are each hydrogen.

In some embodiments of any of the embodiments described herein, Ra is alkyl. In some embodiments, the alkyl is unsubstituted. In some embodiments, Ra is $C_{1-4}$-alkyl, optionally unsubstituted $C_{1-4}$-alkyl. In exemplary embodiments, Ra is methyl.

Compound 1 (also referred to herein interchangeably as MPGL1) is an exemplary compound wherein R is OR' (e.g., wherein R' is methyl):

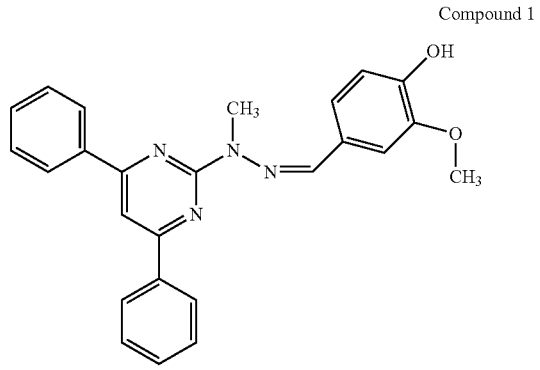 [SMILES: COc1cc(/C=N\N(C)c2nc(-c3ccccc3)cc(-c3ccccc3)n2)ccc1O]

Compound 1

Compound 3 (also referred to herein interchangeably as Compound MK-28) is an exemplary compound wherein R is OH:

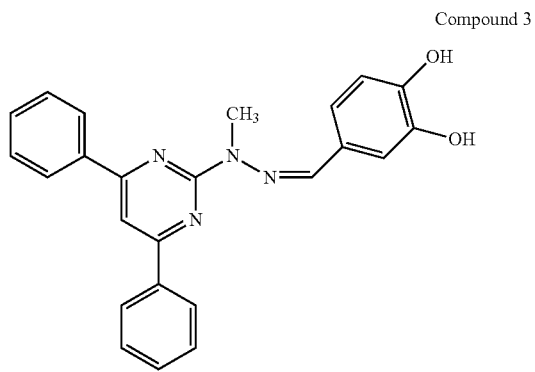 [SMILES: CN(/N=C\c1ccc(O)c(O)c1)c1nc(-c2ccccc2)cc(-c2ccccc2)n1]

Compound 3

As exemplified herein, Compound 3 features enhanced activity relative to the structurally related compounds Compound 1 and A4.

Without being bound by any particular theory, it is believed that the presence of two hydroxy groups in Compound 3, as opposed to one hydroxy group in Compound 1 and A4, enhances activity, for example, by increasing hydrogen bond interactions with the activation loop of PERK.

According to an aspect of some embodiments of the invention, there is provided a compound represented by Formula I, wherein R is OR' and $R_7$ and $R_{12}$ are each hydrogen (according to any of the respective embodiments described herein). In some such embodiments, $R_5$-$R_{14}$ are each hydrogen (according to any of the respective embodiments described herein). In some such embodiments, $R_3$-$R_{14}$ are each hydrogen (according to any of the respective embodiments described herein). In some embodiments, the compound is referred to herein as Compound 1 or as MPGL1.

Compounds (according to any of the aspects described herein) in which one or more of R, $R_1$ and $R_2$ is OH are presented herein as an "enol" tautomer, but can undergo keto-enol tautomerization. Some embodiments of the present invention therefrom encompass also the "keto" tautomer of these compounds.

Exemplary keto-enol tautomers are presented in the following scheme for Compound 3.

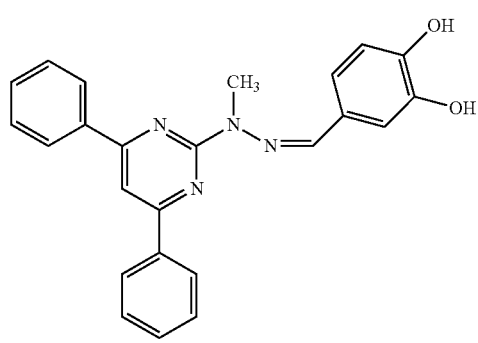 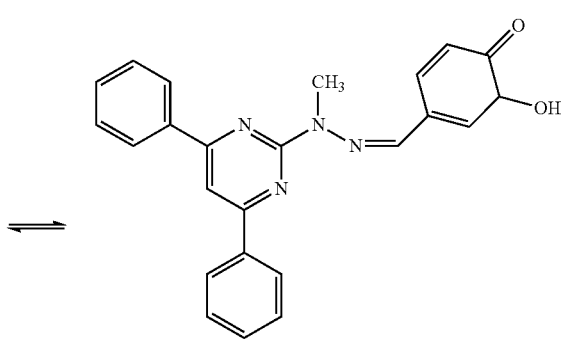

In some embodiments, compounds which present keto-enol tautomerization are in a form of the "enol" tautomer.

For any of the embodiments described herein, the compound described herein may be in a form of a salt, for example, a pharmaceutically acceptable salt, and/or in a form of a prodrug.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound.

In the context of some of the present embodiments, a pharmaceutically acceptable salt of the compounds described herein may optionally be a base addition salt comprising at least one acidic (e.g., phenol) group of the compound which is in a negatively charged form (e.g., wherein the acidic group is deprotonated), in combination with at least one counter-ion, derived from the selected base, that forms a pharmaceutically acceptable salt.

The base addition salts of the compounds described herein may therefore be complexes formed between one or more acidic groups of the drug and one or more equivalents of a base.

The base addition salts may include a variety of organic and inorganic counter-ions and bases, such as, but not limited to, sodium (e.g., by addition of NaOH), potassium (e.g., by addition of KOH), calcium (e.g., by addition of $Ca(OH)_2$, magnesium (e.g., by addition of $Mg(OH)_2$), aluminum (e.g., by addition of $Al(OH)_3$ and ammonium (e.g., by addition of ammonia). Each of these acid addition salts can be either a mono-addition salt or a poly-addition salt, as these terms are defined herein.

Alternatively or additionally, a pharmaceutically acceptable salt of the compounds described herein may optionally be an acid addition salt comprising at least one basic (e.g., nitrogen-containing) group of the compound which is in a positively charged form (e.g., wherein the basic group is protonated), in combination with at least one counter-ion, derived from the selected acid, that forms a pharmaceutically acceptable salt.

The acid salts of the compounds described herein may therefore be complexes formed between one or more basic groups of the drug and one or more equivalents of an acid.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined hereinabove.

Depending on the stoichiometric proportions between the charged group(s) in the compound and the counter-ion in the salt, the acid or base additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

As used herein, the term "prodrug" refers to a compound which is converted in the body to an active compound (e.g., the compound of the formula described hereinabove). A prodrug is typically designed to facilitate administration, e.g., by enhancing absorption. A prodrug may comprise, for example, the active compound modified with ester groups, for example, wherein any one or more of the hydroxyl groups of a compound is modified by an acyl group, optionally $(C_{1-4})$acyl (e.g., acetyl) group to form an ester group, and/or any one or more of the carboxylic acid groups of the compound is modified by an alkoxy or aryloxy group, optionally $(C_{1-4})$alkoxy (e.g., methyl, ethyl) group to form an ester group.

Further, each of the compounds described herein, including the salts thereof, can be in a form of a solvate or a hydrate thereof.

The term "solvate" refers to a complex of variable stoichiometry (e.g., di-, tri-, tetra-, penta-, hexa-, and so on), which is formed by a solute (the heterocyclic compounds described herein) and a solvent, whereby the solvent does not interfere with the biological activity of the solute.

The term "hydrate" refers to a solvate, as defined hereinabove, where the solvent is water.

The present embodiments further encompass any isomorph thereof.

The terms "hydroxyl" or "hydroxy", as used herein, refer to an —OH group.

The term "thiohydroxy", as used herein, refers to an —SH group.

As used herein, the term "amine" describes a —NR'R" group where each of R' and R" is independently hydrogen, alkyl, cycloalkyl, heteroalicyclic, aryl or heteroaryl, as these terms are defined herein. An amine in which one of R' and R" is other than hydrogen may also referred to herein as "modified amine".

As used herein, the term "alkyl" describes an aliphatic hydrocarbon including straight chain and branched chain groups. The alkyl may have 1 to 20 carbon atoms, or 1-10 carbon atoms, and may be branched or unbranched. According to some embodiments of the present invention, the alkyl is a low (or lower) alkyl, having 1-4 carbon atoms (namely, methyl, ethyl, propyl and butyl).

Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. In some embodiments, the alkyl is a lower alkyl, including 1-6 or 1-4 carbon atoms.

An alkyl can be substituted or unsubstituted. When substituted, the substituent can be, for example, one or more of a cycloalkyl, aryl, heteroaryl, heteroalicyclic, halo (e.g., forming a trihaloalkyl, as defined herein), hydroxy, alkoxy, sulfonate, sulfoxide, thiosulfate, sulfate, sulfite, thiosulfite, phosphonate, thiohydroxy, thioalkoxy, cyano, nitro, azo, sulfonamide, carbonyl, thiocarbonyl, C-carboxylate, O-carboxylate, N-thiocarbamate, O-thiocarbamate, oxo, thiooxo, oxime, acyl halide, azide, urea, thiourea, N-carbamate, O-carbamate, C-amide, N-amide, hydrazine or hydrazide, as these terms are defined herein. An alkyl substituted by aryl is also referred to herein as "alkaryl", an example of which is benzyl.

In any of the embodiments described herein wherein an "alkyl" is described, it is to be understood that the alkyl may optionally be replaced by alkenyl or alkynyl. Thus, term "alkyl" as used herein, also encompasses saturated or unsaturated hydrocarbon, thereby encompassing alkenyl and alkynyl, unless indicated otherwise (e.g., wherein alkenyl and/or alkynyl are explicitly listed as alternatives to alkyl).

The term "alkenyl" describes an unsaturated alkyl, as defined herein, having at least two carbon atoms and at least one carbon-carbon double bond, e.g., allyl, vinyl, 3-butenyl, 2-butenyl, 2-hexenyl and i-propenyl. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "halo" as used herein refers to F, Cl, Br and I atoms as substituents.

The term "cycloalkyl" refers to an all-carbon monocyclic or fused ring (i.e., rings which share an adjacent pair of carbon atoms), branched or unbranched group containing 3 or more carbon atoms where one or more of the rings does not have a completely conjugated pi-electron system, and may further be substituted or unsubstituted. Exemplary cycloalkyl groups include, for example, cyclopropyl, cyclobutyl, cyclopentyl, cyclohexyl, or cyclododecyl. The cycloalkyl can be substituted or unsubstituted. When substituted, the substituent can be, for example, one or more of an alkyl, alkenyl, alkynyl, cycloalkyl, aryl, heteroaryl, heteroalicyclic, halo, hydroxy, alkoxy, sulfonate, sulfoxide, thiosulfate, sulfate, sulfite, thiosulfite, phosphonate, thiohydroxy, thioalkoxy, cyano, nitro, azo, sulfonamide, carbonyl, thiocarbonyl, C-carboxylate, O-carboxylate, N-thiocarbamate, O-thiocarbamate, oxo, thiooxo, oxime, acyl halide, azide, urea, thiourea, N-carbamate, O-carbamate, C-amide, N-amide, hydrazine or hydrazide, as these terms are defined herein below.

The term "aryl" describes an all-carbon monocyclic or fused-ring polycyclic (i.e., rings which share adjacent pairs of carbon atoms) groups having a completely conjugated pi-electron system. The aryl group may be unsubstituted or substituted by one or more substituents. When substituted, the substituent can be, for example, one or more of an alkyl, alkenyl, alkynyl, cycloalkyl, aryl, heteroaryl, heteroalicyclic, halo, hydroxy, alkoxy, sulfonate, sulfoxide, thiosulfate, sulfate, sulfite, thiosulfite, phosphonate, thiohydroxy, thioalkoxy, cyano, nitro, azo, sulfonamide, carbonyl, thiocarbonyl, C-carboxylate, O-carboxylate, N-thiocarbamate, O-thiocarbamate, acyl halide, azide, urea, thiourea, N-carbamate, O-carbamate, C-amide, N-amide, hydrazine or hydrazide, as these terms are defined herein below.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. Representative examples are thiadiazole, pyridine, pyrrole, oxazole, indole, purine and the like. The heteroaryl group may be unsubstituted or substituted by one or more substituents. When substituted, the substituent can be, for example, one or more of an alkyl, alkenyl, alkynyl, cycloalkyl, aryl, heteroaryl, heteroalicyclic, halo, hydroxy, alkoxy, sulfonate, sulfoxide, thiosulfate, sulfate, sulfite, thiosulfite, phosphonate, thiohydroxy, thioalkoxy, cyano, nitro, azo, sulfonamide, carbonyl, thiocarbonyl, C-carboxylate, O-carboxylate, N-thiocarbamate, O-thiocarbamate, oxo, thiooxo, oxime, acyl halide, azide, urea, thiourea, N-carbamate, O-carbamate, C-amide, N-amide, hydrazine or hydrazide, as these terms are defined herein below.

The term "heteroalicyclic", as used herein, describes a monocyclic or fused ring group having in the ring(s) one or more atoms such as nitrogen, oxygen and sulfur. The rings may also have one or more double bonds. However, the rings do not have a completely conjugated pi-electron system. Representative examples are morpholine, piperidine, piperazine, tetrahydrofurane, tetrahydropyrane and the like. The heteroalicyclic may be substituted or unsubstituted. When substituted, the substituent can be, for example, one or more of an alkyl, alkenyl, alkynyl, cycloalkyl, aryl, heteroaryl, heteroalicyclic, halo, hydroxy, alkoxy, sulfonate, sulfoxide, thiosulfate, sulfate, sulfite, thiosulfite, phosphonate, thiohydroxy, thioalkoxy, cyano, nitro, azo, sulfonamide, carbonyl, thiocarbonyl, C-carboxylate, O-carboxylate, N-thiocarbamate, O-thiocarbamate, oxo, thiooxo, oxime, acyl halide, azide, urea, thiourea, N-carbamate, O-carbamate, C-amide, N-amide, hydrazine or hydrazide, as these terms are defined herein below.

The term "alkoxy" refers to an —O-alkyl, —O-cycloalkyl, —O-heteroalicyclic, —O-aryl or —O-heteroaryl group, as defined herein.

The term "thioalkoxy" refers to an —S-alkyl, —S-cycloalkyl, —S-heteroalicyclic, —S-aryl or —S-heteroaryl group, as defined herein.

The term "hydroxyalkyl" as used herein, refers to an alkyl group, as defined herein, substituted with one or more hydroxy group(s), e.g., hydroxymethyl, 2-hydroxyethyl and 4-hydroxypentyl.

The term "trihaloalkyl" refers to —CX$_3$, wherein X is halo, as defined herein. An exemplary haloalkyl is CF$_3$.

A "guanidino" or "guanidine" or "guanidinyl" group refers to an —RaNC(=NRd)—NRbRc group, where each of Ra, Rb, Rc and Rd can be as defined herein for R' and R".

A "guanyl" or "guanine" group refers to an R'R"NC(=NR'")— group, where R', R" and R'" are as defined herein.

In some of any of the embodiments described herein, the guanidine group is —NH—C(=NH)—NH$_2$.

In some of any of the embodiments described herein, the guanyl group is H$_2$N—C(=NH)— group.

Any one of the amine (including modified amine), guanidine and guanine groups described herein is presented as a free base form thereof, but is meant to encompass an ionized form thereof at physiological pH, and/or within a salt thereof, e.g., a pharmaceutically acceptable salt thereof, as described herein.

The term "cyano" describes a —CN group.

The term "nitro" describes an —NO$_2$ group.

The term "sulfate" describes a —O—S(=O)$_2$—OR' group, where R' is as defined hereinabove.

The term "thiosulfate" describes a —O—S(=S)(=O)—OR' group, where R' is as defined hereinabove.

The term "sulfite" describes an —O—S(=O)—O—R' group, where R' is as defined hereinabove.

The term "thiosulfite" describes a —O—S(=S)—O—R' group, where R' is as defined hereinabove.

The term "sulfinate" describes a —S(=O)—OR' group, where R' is as defined hereinabove.

The term "sulfoxide" or "sulfinyl" describes a —S(=O)R' group, where R' is as defined hereinabove.

The term "sulfonate" describes a —S(=O)$_2$—R' group, where R' is as defined herein.

The term "S-sulfonamide" describes a —S(=O)$_2$—NR'R" group, with R' and R" as defined herein.

The term "N-sulfonamide" describes an R'S(=O)$_2$—NR"— group, where R' and R" are as defined herein.

The term "phosphonate" describes a —P(OR')(OR")OR''' group, where R', R" and R''' are as defined herein.

The term "carbonyl", "carbonate" or "acyl" as used herein, describes a —C(=O)—R' group, with R' as defined herein.

The term "acyl halide" describes a —(C=O)R"" group wherein R"" is halide. The term "thiocarbonyl" as used herein, describes a —C(=S)—R' group, with R' as defined herein.

The term "oxo" as used herein, describes a (=O) group, wherein an oxygen atom is linked by a double bond to the atom (e.g., carbon atom) at the indicated position.

The term "thiooxo" as used herein, describes a (=S) group, wherein a sulfur atom is linked by a double bond to the atom (e.g., carbon atom) at the indicated position.

The term "oxime" describes a =N—OH group.

The term "azo" or "diazo" describes an —N=NR' group, with R' as defined hereinabove.

The term "azide" describes an —N$_3$ group.

The term "carboxylate" as used herein encompasses C-carboxylate and O-carboxylate.

The term "C-carboxylate" describes a —C(=O)—OR' group, where R' is as defined herein.

The term "O-carboxylate" describes a —OC(=O)R' group, where R' is as defined herein.

A carboxylate can be linear or cyclic. When cyclic, R' and the carbon atom are linked together to form a ring, in C-carboxylate, and this group is also referred to as lactone. Alternatively, R' and O are linked together to form a ring in O-carboxylate.

The term "carbamate" as used herein encompasses N-carbamate and O-carbamate.

The term "N-carbamate" describes an R"OC(=O)—NR'— group, with R' and R" as defined herein.

The term "O-carbamate" describes an —OC(=O)—NR'R" group, with R' and R" as defined herein.

A carbamate can be linear or cyclic. When cyclic, R' and the carbon atom are linked together to form a ring, in O-carbamate. Alternatively, R' and O are linked together to form a ring in N-carbamate.

The term "thiocarbamate" as used herein encompasses N-thiocarbamate and O-thiocarbamate.

The term "O-thiocarbamate" describes a —OC(=S)—NR'R" group, with R' and R" as defined herein.

The term "N-thiocarbamate" describes an R"OC(=S)NR'— group, with R' and R" as defined herein.

Thiocarbamates can be linear or cyclic, as described herein for carbamates.

The term "dithiocarbamate" as used herein encompasses S-dithiocarbamate and N-dithiocarbamate.

The term "S-dithiocarbamate" describes a —SC(=S)—NR'R" group, with R' and R" as defined herein.

The term "N-dithiocarbamate" describes an R"SC(=S)NR'— group, with R' and R" as defined herein.

The term "urea" describes a —NR'C(=O)—NR"R''' group, where R' and R" are as defined herein and R''' is as defined herein for R' and R".

The term "thiourea" describes a —NR'—C(=S)—NR"R''' group, with R', R" and R''' as defined herein.

The term "amide" as used herein encompasses C-amide and N-amide.

The term "C-amide" describes a —C(=O)—NR'R" group, where R' and R" are as defined herein.

The term "N-amide" describes a R'C(=O)—NR"— group, where R' and R" are as defined herein.

The term "hydrazine" describes a —NR'—NR"R''' group, with R', R", and R''' as defined herein.

As used herein, the term "hydrazide" describes a —C(=O)—NR'—NR"R''' group, where R', R" and R''' are as defined herein.

According to an aspect of some embodiments of the invention, there is provided a process of preparing a compound according to any of the embodiments described herein, the process comprising reacting a first precursor compound comprising a diphenylpyridyl hydrazine (with suitable Ra and R$_{5-14}$ groups) and a second precursor which is a benzaldehyde with suitable R and R$_{1-4}$ groups (attached to the phenyl moiety of the benzaldehyde). The process may optionally be effected using procedures exemplified in Example 1 described herein.

Uses and Indications:

A compound according to any of the embodiments described herein (e.g., in the section relating to compounds) may optionally be used in the context of any one or more of the uses, indications and/or methods described as follows.

In some embodiments, the compound according to any one of the embodiments described herein is a compound capable of inhibiting PERK.

In some embodiments, the compound according to any one of the embodiments described herein is for use in inhibiting an activity of PERK.

Herein and in the art, the term "PERK" refers to a protein also known as "PKR-like endoplasmic reticulum kinase" and "eIF2αK3" (eIF2α kinase 3).

An exemplary activity of PERK (which may be inhibited according to some embodiments described herein) is phosphorylation of eIF2α.

In some of any of the embodiments described herein relating to PERK inhibition, the PERK inhibition is partial, e.g., an activity of PERK is reduced by about 20%, 30%, 40%, 50%, 60% or 70%, or 80%, including any intermediate value therebetween, in the presence of a compound as described herein.

In some of any of the embodiments described herein relating to PERK inhibition, the PERK inhibition is such that improves viability of cells exerting imbalanced PERK activity.

According to an aspect of some embodiments of the present invention, there is provided a method of inhibiting an activity of PERK, the method comprising contacting the PERK with a compound according to any of the embodiments described herein.

In some embodiments of any of the embodiments relating to a use and/or method for inhibiting an activity of PERK, the use and/or method is effected in vivo, for example, by administering a therapeutically effective amount of the compound to a subject in need thereof.

As used herein, the phrase "therapeutically effective amount" describes a dose of an active ingredient or a composition comprising the active ingredient that will provide the therapeutic effect for which the active ingredient is indicated (for example, inhibiting or partially inhibiting an activity of PERK), optionally by relieving to some extent one or more of the symptoms of a condition being treated (e.g., according to any of the respective embodiments described herein.

In some embodiments, the use and/or method for inhibiting an activity of PERK is effected ex vivo (e.g., in vitro), for example, in research.

In some embodiments, the compound according to any one of the embodiments described herein is for use in treating a disease or disorder in which inhibition of PERK is beneficial.

Herein, the term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

According to an aspect of some embodiments of the present invention, there is provided a use of a compound according to any one of the embodiments described herein in the manufacture of a medicament for inhibiting an activity of PERK.

According to an aspect of some embodiments of the present invention, there is provided a use of a compound according to any one of the embodiments described herein in the manufacture of a medicament for treating a disease or disorder in which inhibition of PERK is beneficial.

According to an aspect of some embodiments of the present invention, there is provided a method of treating a disease or disorder in which inhibition of PERK is beneficial, the method comprising administering to a subject in need thereof a therapeutically effective amount of a compound according to any one of the embodiments described herein.

Diseases in which such inhibition of PERK is beneficial (in the context of any of the respective embodiments described herein) include, for example, neurodegenerative diseases and disorders.

Examples of neurodegenerative diseases and disorders treatable by a compound described herein include, without limitation, Huntington's disease; Alzheimer's disease; Parkinson's disease; amyotrophic lateral sclerosis (ALS); prion disease (e.g., Creutzfeldt-Jakob disease, scrapie); Lewy-body dementia; spongiform encephalopathies; multiple sclerosis; glutamate neurotoxicity; motor neuron disease; restless legs syndrome (RLS) migraine; neurodegenerative disease or disorder associated with traumatic injury (e.g., concussion, blast injury and/or combat-related injury), bacterial and/or viral infection, ischemia and/or hypoxia (e.g., cerebral ischemia, ischemic/reperfusion injury in stroke, myocardial ischemia and/or renal ischemia); platelet aggregation, heart attack, cardiac hypertrophy, atherosclerosis and/or arteriosclerosis; spinal cord injury (e.g., partial or total spinal cord transection); frontotemporal dementias; AIDS-associated dementia; ataxias; and memory deficiencies (e.g., long-term memory impairment).

Without being bound by any particular theory, it is believed that compounds disclosed herein are cell-permeable small molecules, capable of reducing cytotoxicity induced by causes of ER stress—for example, pathogenic huntingtin mutant—to thereby rescue cells (e.g., striatal cells). It is further believed that such rescue is capable of ameliorating cognitive and motor dysfunctions in diseased subjects.

In some embodiments, the compound according to any one of the embodiments described herein is for use in downregulating an unfolded protein response (UPR), for example, in a cell.

Herein, the terms "unfolded protein response" and "UPR" refer to a cellular stress response associated with endoplasmic reticulum (ER) stress, which includes at least three components that counteract ER stress: stress gene expression, translational attenuation, and ER-associated protein degradation (ERAD). UPR typically includes activity by the transducer proteins XBP1, ATF6 and PERK.

Herein, "downregulating" an unfolded protein response means reducing a degree of any (optionally all) of the processes and/or protein activities encompassed by an unfolded protein response, for example, by reducing an amount of a protein involved in the unfolded protein response and/or by inhibiting the protein. Downregulating may optionally be effected on the genomic and/or the transcript level by interfering with transcription and/or translation of one or more proteins involved in an unfolded protein response; and/or on the protein level by inactivating one or more proteins involved in an unfolded protein response (e.g., by phosphorylation/dephosphorylation, antagonism, cleavage of the protein, and the like).

Downregulation of a UPR may optionally be determined as a reduction in phosphorylation of eIF2α, for example, in the presence of a condition or compound (e.g., tunicamycin) which induces EPR (e.g., as exemplified herein).

According to an aspect of some embodiments of the present invention, there is provided a method of downregulating an unfolded protein response in a cell, the method comprising contacting the cell with a compound according to any of the embodiments described herein.

In some embodiments of any of the embodiments relating to a use and/or method for downregulating an unfolded protein response in a cell, the use and/or method is effected in vivo, for example, by administering a therapeutically effective amount of the compound to a subject in need thereof.

In some embodiments, the use and/or method for downregulating an unfolded protein response in a cell is effected ex vivo (e.g., in vitro), for example, in research.

In some embodiments, the compound according to any one of the embodiments described herein is for use in treating a disease or disorder in which downregulating an unfolded protein response is beneficial.

According to an aspect of some embodiments of the present invention, there is provided a use of a compound according to any one of the embodiments described herein in the manufacture of a medicament for downregulating an unfolded protein response.

According to an aspect of some embodiments of the present invention, there is provided a use of a compound according to any one of the embodiments described herein in the manufacture of a medicament for treating a disease or disorder in which downregulating an unfolded protein response is beneficial.

According to an aspect of some embodiments of the present invention, there is provided a method of treating a disease or disorder in which downregulating an unfolded protein response is beneficial, the method comprising administering to a subject in need thereof a therapeutically effective amount of a compound according to any one of the embodiments described herein.

Examples of diseases or disorders in which downregulating an unfolded protein response is beneficial include, without limitation, Alzheimer's disease, Parkinson's disease, Huntington's disease and prion disease (e.g., Creutzfeldt-Jakob disease).

In some embodiments, the compound according to any one of the embodiments described herein is for use in treating a disease or disorder associated with ER (endoplasmic reticulum) stress and/or aggregation-prone proteins.

According to an aspect of some embodiments of the present invention, there is provided a use of a compound according to any one of the embodiments described herein in the manufacture of a medicament for treating a disease or disorder associated with ER stress and/or aggregation-prone proteins.

According to an aspect of some embodiments of the present invention, there is provided a method of treating disease or disorder associated with ER stress and/or aggregation-prone proteins, the method comprising administering to a subject in need thereof a therapeutically effective amount of a compound according to any one of the embodiments described herein.

Herein and in the art, the term "ER stress" relates to any internal or external cellular stimulus that compromises ER (endoplasmic reticulum) homeostasis by stressing the protein folding capacity of the ER. Cells typically cope with ER stress by activating the unfolded protein response (UPR), as described herein. The cellular response to ER stress may optionally include formation of protein aggregates referred to in the art as stress granules (SGs), typically 100-200 nm in size, not surrounded by a membrane and associated with the endoplasmic reticulum. Stress granules can be identified using methods known in the art.

A cell may optionally be regarded as being in stress if there is presence of stress granules, or if there is an elevation of at least 5%, 10%, 20%, 30%, 40%, 50% or more in stress granules in the cell as compared to another cell of the same species, type, developmental stage and growth conditions only not subjected to conditions associated with stress.

Examples of aggregation-prone proteins (also referred to herein and in the art as aggregation-forming proteins) include, but are not limited to, Z alpha1-antitrypsin, alpha-synuclein, tau, beta amyloid, SOD1, prion protein (prp), neuroserpin, islet amyloid protein (IAPP), ataxins (1-7), androgen receptor, atrophin 1, huntingtin and other polyglutamine repeat proteins, HOXD13 (synpolydactyly) and other polyalanine repeat proteins.

Examples of diseases or disorders associated with aggregation-prone proteins include, without limitation, Huntington's disease, amyloidosis, cataract, type II diabetes, cancer and memory deficiency (e.g., long-term memory impairment).

In some embodiments, the compound according to any one of the embodiments described herein is for use in treating Huntington's disease.

According to an aspect of some embodiments of the present invention, there is provided a use of a compound according to any one of the embodiments described herein in the manufacture of a medicament for treating Huntington's disease.

According to an aspect of some embodiments of the present invention, there is provided a method of treating Huntington's disease, the method comprising administering to a subject in need thereof a therapeutically effective amount of a compound according to any one of the embodiments described herein.

Further examples (in addition to Huntington's disease) of diseases or disorders that are treatable by compounds described herein (according to any of the respective embodiments described herein) include, without limitation, other neurodegenerative diseases and disorders such as, but not limited to, Alzheimer's disease, Parkinson's disease, amyotrophic lateral sclerosis (ALS), prion disease, Lewy-body dementia, spongiform encephalopathies, frontotemporal dementias, and ataxias; as well as other conditions involving protein aggregation such as, for example, amyloidosis, cataract, type II diabetes, cancer and memory deficiency (e.g., long term memory impairment).

Formulation:

The compounds described herein can be used per se or as a part of a pharmaceutical composition which further comprises a pharmaceutically acceptable carrier.

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

In some embodiments, the compound and/or pharmaceutical composition are administered via systemic administration (according to any of the respective embodiments described herein).

Alternatively, one may administer the compound and/or pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations, which can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

As exemplified herein, compounds according to some embodiments described herein are naturally capable of crossing the BBB (e.g., upon systemic administration), for example, such that higher concentrations are of the compound are achieved in the CNS (e.g., brain) than in plasma.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (a compound as described herein) effective to prevent, alleviate or ameliorate symptoms of a disorder (e.g., Huntington's disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide levels of the active ingredient at the diseased tissue that are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single administration or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

Treatment of any of the conditions described herein with a compound described herein (according to any of the respective embodiments described herein) may optionally be further comprise co-administration of one or more additional agent for treating the condition (e.g., an agent known in the art to be useful in treating the condition). The additional agent can be co-administered prior to, concomitantly or subsequent to administering the compound of the present invention.

A pharmaceutical composition according to some embodiments of any of the embodiments described herein further comprises, in addition to a compound and carrier described herein, one or more additional agent useful for treating a condition described herein (according to any of the respective embodiments).

As used herein the term "about" refers to ±10%, and in some embodiments the term "about" refers to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:
Tunicamycin (Tun), PKR inhibitor (PKRi), poly-LC and other common reagents were obtained from Sigma.

PERK inhibitor A4 [Wang et al., *Chem Biol Drug Des* 2010, 76: 480-495] was obtained from ChemBridge Chemical Store.

Antibodies:
Rabbit anti-phospho-eIF2α (Ser51) and mouse anti-total eIF2α were obtained from Cell Signaling.

Mouse anti-GAPDH was obtained from Chemicon International.

Goat anti-rabbit and anti-mouse IgG conjugated to HRP were obtained from Jackson Labs.

Cell culture and transfections: STHdhQ7/7 and STHdhQ111/111 cells were grown as described in Leitman et al. [*PLoS One* 2014, 9(3):e90803].

Treatments and immunoblotting: Cells were treated with Tun (5 μg/ml) or with A4, PKRi, poly-LC or exemplary PERK inhibitors of the present embodiments, by adding the tested compound to the cell medium at the indicated concentrations and times. Cell lysis and immunoblotting was performed as described in Leitman et al. [*PLoS One* 2014, 9(3):e90803].

Cell Cycle FACS analysis: After the indicated treatment times in full medium or in DMEM without serum, cells were incubated with propidium iodide (PI) solution (10 μg/ml) and read by flow cytometry as described in Leitman et al. [*PLoS One* 2014, 9(3):e90803]. Cells in sub-G0/G1 were counted as apoptotic/dead cells.

Mouse HD model: The HD mouse model used was the R6/2 transgenic mice model B6CBA-R6/2 (CAG 160) Jackson Lab USA. R6/2 mice express only the exon 1 of the human Htt gene, including 150 CAG repeats driven by the human Htt promoter directly influencing the transgene expression levels and thereby the development of HD-like pathology. Out of all the existing mouse models of HD, the R6/2 mouse is one that develops symptoms the most rapidly and has the most widespread occurrence of Htt inclusions in the brain. Furthermore, these lines are the most widely used in therapeutic trials. In these animals, the initial signs of motor symptoms commence around 3 weeks of age. The mice display locomotor hyperactivity and shortly thereafter, they exhibit the first signs of impairments of learning and memory, which gradually become worse up to the age of 7 weeks. While R6/2 mice are initially hyperactive, they gradually reduce their motor activity and become hypoactive around 8 weeks of age. Their motor function and coordination progressively deteriorate, and can be detected as a reduction in the time they can stay on a rotating rod, the so-called Rotarod. Typically, R6/2 mice are severely impaired by 8-12 weeks of age and most colonies die at around 13-16 weeks of age.

Study Groups: Treated R6/2 mice were compared with untreated and with treated and untreated control WT (wild-type) littermates, in four groups of 18 mice/each. A group of WT without the Alzet pump was also added.

Rotarod test: Motor activity was assessed by the rotarod test using the San Diego Instrument, Rotor-Rod (San Diego Instruments, CA, USA) (0-25 RPM). R6/2 mice and controls were tested every week after pump transplantation. Each test consisted of 3 consecutive measurements of 5 minutes on 4 rpm, 60 minutes of rest, 3 times 0-40 rpm. The latency to fall was recorded.

Limb clasping: Hind-limb clasping behavior was scored on a scale from 0 to 3: 0=normal; 1=clasps hind limbs within 30 seconds of being suspended in the air; 2=clasps hind limbs within 5 seconds but recovers quickly when released after 30 seconds; 3=clasps hind limbs within 5 seconds and has difficulty recovering when released after 30 seconds.

Ledge test: The ledge test is a direct measure of coordination. Mice were lifted from the cage and placed on the cage's ledge. Mice will typically walk along the ledge and attempt to descend back into the cage. Walking along the ledge without losing its balance is assigned a score of 0. If the mouse loses its footing while walking along the ledge, it receives a score of 1. If it does not effectively use its hind legs, or lands on its head rather than its paws when descending into the cage, it receives a score of 2. If it falls off the ledge, or nearly so, while walking or attempting to lower itself, or shakes and refuses to move at all despite encouragement, it receives a score of 3.

Gait: Gait is a measure of coordination and muscle function. If the mouse moves normally, with its body weight supported on all limbs, with its abdomen not touching the ground, and with both hindlimbs participating evenly, it receives a score of 0. If it shows a limp while walking, it receives a score of 1. If it shows a severe limp, lowered pelvis, it receives a score of 2. If the mouse has difficulty moving forward and drags its abdomen along the ground, it receives a score of 3.

Kyphosis: Kyphosis is a characteristic dorsal curvature of the spine that is a common manifestation of neurodegenerative disease in mouse models. It is caused by a loss of muscle tone in the spinal muscles secondary to neurodegeneration. If the mouse is able to easily straighten its spine as it walks, and does not have persistent kyphosis, it receives a score of 0. If the mouse exhibits mild kyphosis but is able to straighten its spine, it receives a score of 1. If it is unable to straighten its spine completely and maintains persistent but mild kyphosis, it receives a score of 2. If the mouse maintains pronounced kyphosis as it walks or while it sits, it is assigned a score of 3.

Statistical Analysis:

Generally, the results are expressed as mean±standard error unless otherwise stated. Student's t-test was used to compare the means of two groups. Comparisons between several groups were performed using ANOVA with Scheffe post hoc analysis. Repeated tests (weekly rotarod) were also analyzed using the repeated measurement ANOVA test.

Example 1

Chemical Syntheses

Derivatives of the previously reported A4 PERK inhibitor [Wang et al., *Chem Biol Drug Des* 2010, 76: 480-495] were designed and synthesized, using, as starting materials, compounds structurally related to the compounds used for preparing A4 (vanillin, an aromatic aldehyde, and a 1,1-disubstituted hydrazine, bearing a diarylpyrimidine substituent) while forming the hydrazone bond of A4.

The designed compounds included elimination of the bulky bromo substituent present in A4 as a means to increase activity (see, Compound 1; MPGL1). Other substitutions were made as detailed hereinafter, producing a series of compounds, denoted herein Compounds 2-5, as depicted below. High yields of over 80% were obtained for most compounds.

General Procedure for the Preparation of Compounds 1-5:

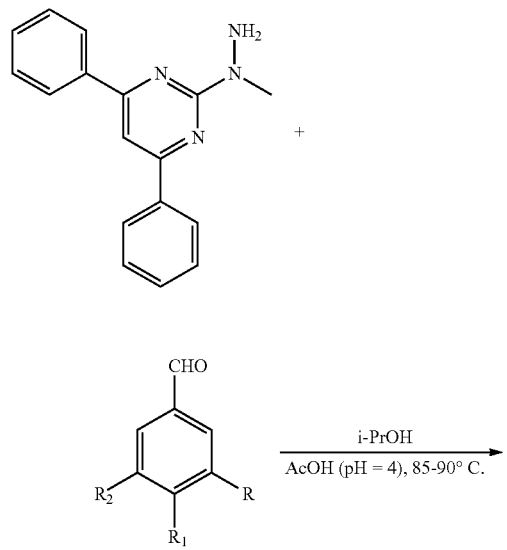

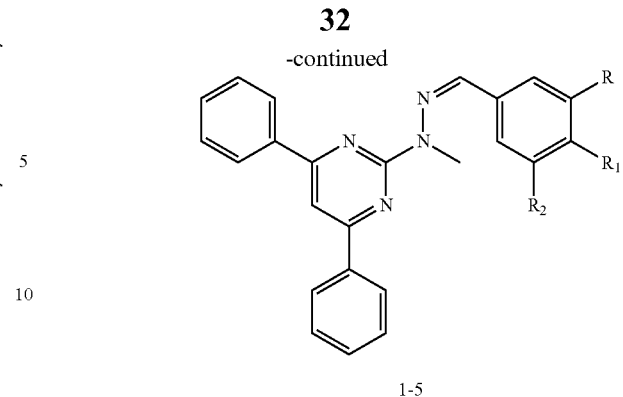

1-5

To a suspension of 2-(N-methylhydrazino)-4,6-diphenylpyrimidine (1 equivalent) in isopropyl alcohol (7-8 mL) was added the corresponding substituted benzaldehyde (2 equivalents). Acetic acid was then added until pH 4 was reached, and the reaction mixture was refluxed for 2 hours, until TLC (using dichloromethane; DCM, as eluent) indicated disappearance of the starting materials and the formation of the product. After cooling the reaction mixture in refrigerator overnight, the resultant yellow precipitate was filtered off, washed with cold isopropanol and dried under high vacuum.

Synthesis of 2-{N-methyl-N'-(3-methoxy-4-hydroxybenzylidene)hydrazinyl}-4,6-diphenylpyrimidine (Compound 1; MPGL1)

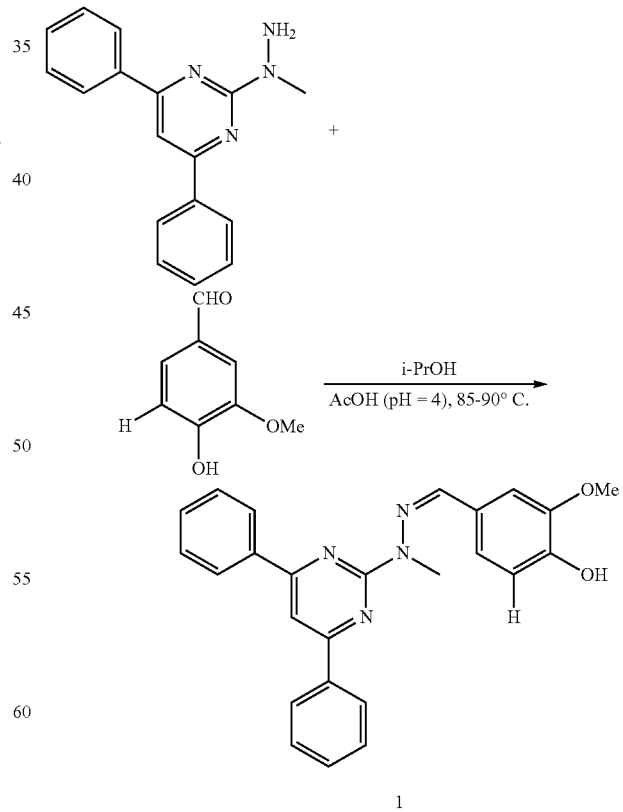

1

Compound 1 (MPGL1) was synthesized by refluxing 2-(N-methylhydrazino)-4,6-diphenylpyrimidine (0.13 gram, 0.45 mmol, 1 equivalent) and 3-methoxy-4-hydroxybenzaldehyde (vanillin) (0.14 gram, 0.9 mmol, 2 equivalents) in 8 mL isopropanol in the presence of the AcOH, as described under the general procedure hereinabove. The yield of light yellow crystals of Compound 1 was 0.15 gram (80%).

$^1$H NMR (400 MHz, DMSO-d$^6$) δ: 9.36 (br s, 1H), 8.45 (d, J=5.8 Hz, 4H), 8.10 (s, 1H), 7.95 (s, 1H), 7.58 (m, 6H), 7.17 (d, J=8.1 Hz, 1H), 6.86 (d, J=8.0 Hz, 1H), 3.93 (s, 3H), 3.79 (s, 3H).

$^{13}$C NMR (100 MHz, DMSO-d$^6$) δ: 165.7, 149.4, 148.7, 138.7, 138.1, 132.2, 129.9, 128.3, 122.5, 56.4, 32.8, 26.7.

Synthesis of 2-{N-methyl-N'-(3,5-dimethoxybenzylidene)hydrazinyl}-4,6-diphenylpyrimidine (Compound 2; MK-26)

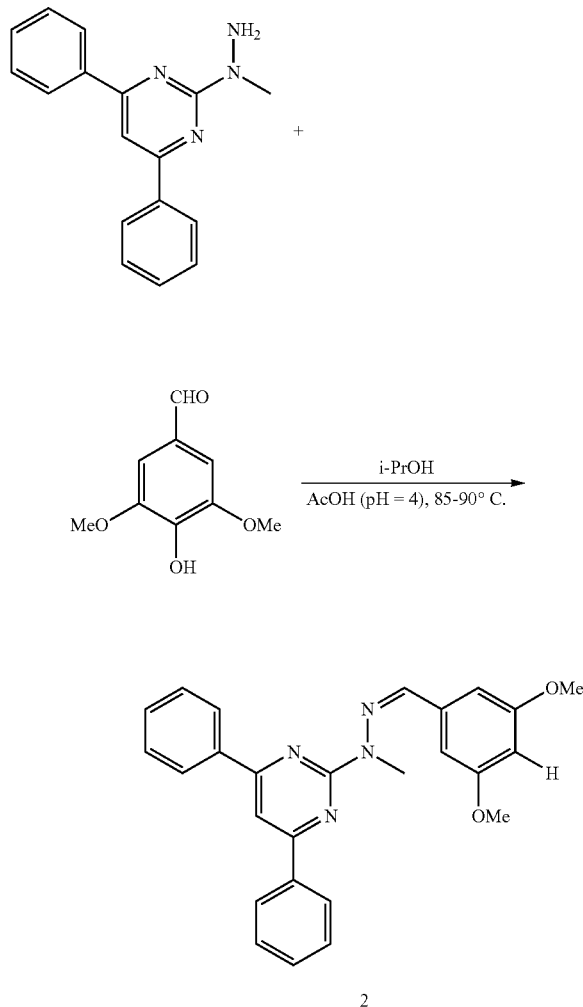

Compound 2 (MK-26) was synthesized from 2-(1-methylhydrazino)-4,6-diphenylpyrimidine (0.1 gram, 0.36 mmol, 1 equivalent) and 3,5-dimethoxybenzaldehyde (0.12 gram, 0.72 mmol, 2 equivalents) in 8 mL isopropanol in the presence of AcOH, as described under the general procedure hereinabove. The yield of white crystals of Compound 2 was 0.13 gram (86%).

$^1$H NMR (400 MHz, DMSO-d$^6$) δ: 8.45 (m, 4H), 8.15 (s, 1H), 7.90 (s, 1H), 7.58 (dd, J=2.0 Hz, J=5.4 Hz, 6H), 7.11 (d, J=2.2 Hz, 2H), 6.50 (t, J=2.2 Hz, J=4.7 Hz, 1H), 3.84 (s, 6H), 3.83 (s, 3H).

$^{13}$C NMR (100 MHz, DMSO-d$^6$) δ: 165.9, 161.1, 137.3, 131.5, 129.3, 127.6, 104.6, 101.6, 55.5, 31.4.

Synthesis of 2-{N-methyl-N'-(3,4-dihydroxybenzylidene)hydrazinyl}-4,6-diphenylpyrimidine (Compound 3; MK-28)

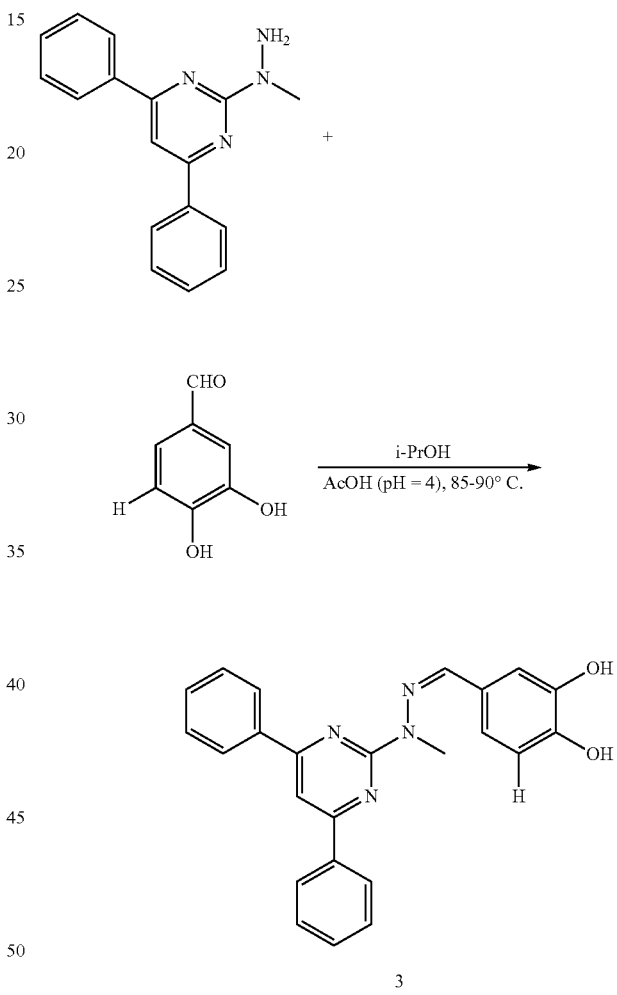

Compound 3 (MK-28) was synthesized from 2-(1-methylhydrazino)-4,6-diphenylpyrimidine (0.1 gram, 0.36 mmol, 1 equivalent) and 3,4-dihydroxybenzaldehyde in 8 mL isopropanol in the presence of AcOH, according to the general procedure described hereinabove. The yield of Compound 3 was 0.12 gram (84%).

$^1$H NMR (400 MHz, DMSO-d$^6$) δ: 9.24 (br s, 1H), 8.41 (m, 4H), 8.06 (s, 1H), 7.90 (s, 1H), 7.60 (dd, J=1.9 Hz, J=5.8 Hz, 6H), 7.39 (d, J=1.9 Hz, 1H), 7.07 (dd, J=1.9 Hz, J=8.2 Hz, 1H), 6.81 (d, J=8.1 Hz, 1H), 3.79 (s, 3H).

$^{13}$C NMR (100 MHz, DMSO-d$^6$) δ: 165.9, 147.9, 146.7, 140.0, 138.2, 132.0, 128.8, 128.4, 120.9, 116.7, 114.1, 104.9, 63.2, 32.4, 26.6.

Synthesis of 2-{N-methyl-N'-(3-hydroxy-4-methoxybenzylidene)hydrazinyl}-4,6-diphenylpyrimidine (Compound 4)

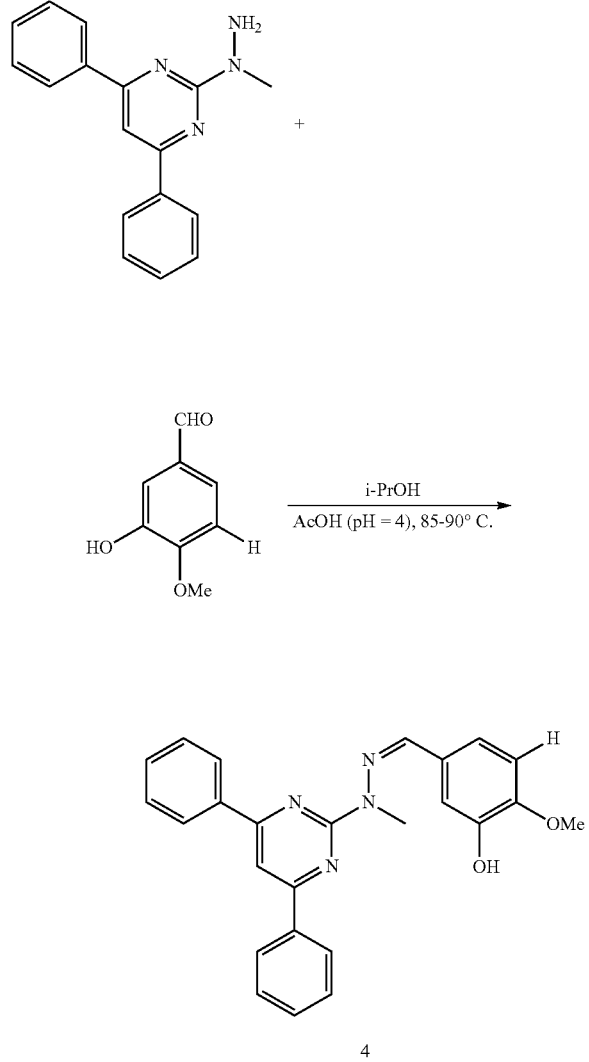

Compound 4 was synthesized from 2-(1-methylhydrazino)-4,6-diphenylpyrimidine (0.1 gram, 0.36 mmol, 1 equivalent) and 3-hydroxy-4-methoxybenzaldehyde (0.115 gram, 0.72 mmol, 2 equivalents) in 8 mL isopropanol in the presence of AcOH, as described under the general procedure hereinabove. The yield of yellow crystals of Compound 4 was 0.1 gram (68%).

$^1$H NMR (400 MHz, DMSO-d$^6$) δ: 9.29 (br s, 1H), 8.42 (m, 4H), 8.08 (s, 1H), 7.94 (s, 1H), 7.58 (m, 6H), 7.42 (d, J=5.1 Hz, 1H), 7.20 (dd, J=2.6 Hz, J=9.1 Hz, 1H), 7.01 (d, J=10.2 Hz, 1H), 4.39 (d, J=5.1 Hz, 1H), 3.82 (d, J=1.7 Hz, 6H).

$^{13}$CNMR (100 MHz, DMSO-d$^6$) δ: 165.9, 162.0, 150.6, 147.9, 140.6, 138.1, 132.1, 130.0, 128.4, 121.2, 114.1, 114.0, 105.7, 63.9, 56.9, 32.8, 26.6.

Synthesis of 2-{N-methyl-N'-(3,5-dimethoxy-4-hydroxybenzylidene)hydrazinyl}-4,6-diphenylpyrimidine (Compound 5)

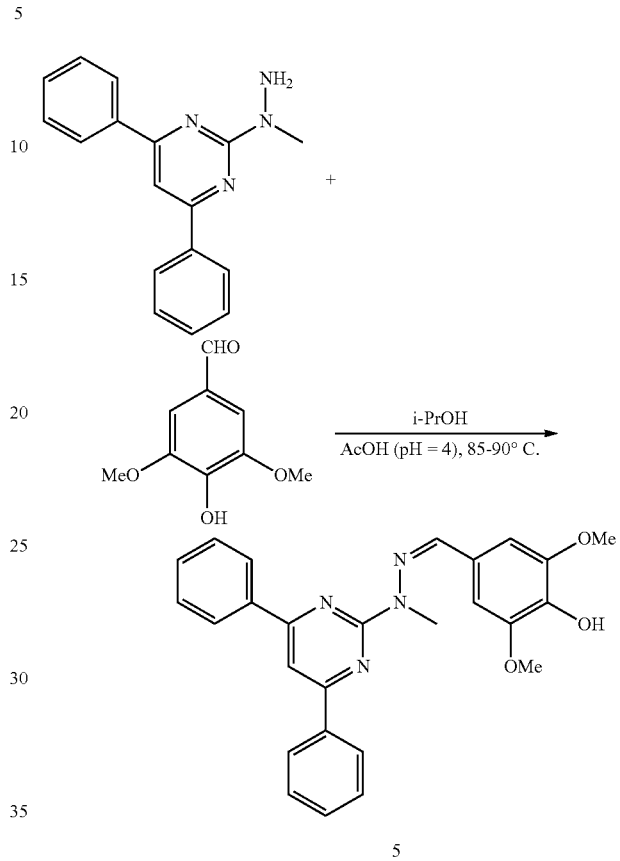

Compound 5 was synthesized from 2-(1-methylhydrazino)-4,6-diphenylpyrimidine (0.1 gram, 0.36 mmol, 1 equivalent) and 3,5-dimethoxy-4-hydroxybenzaldehyde (0.13 gram, 0.72 mmol, 2 equivalents) in 8 mL isopropanol in the presence of AcOH, as described under the general procedure hereinabove. The yield of yellow crystals of Compound 5 was 0.13 gram (82%).

$^1$H NMR (400 MHz, DMSO-d$^6$) δ: 8.71 (br s, 1H), 8.43 (m, 4H), 8.09 (s, 1H), 7.93 (s, 1H), 7.56 (dd, J=1.8 Hz, J=5.2 Hz, 6H), 7.22 (s, 2H), 3.89 (s, 6H), 3.81 (s, 3H).

$^{13}$C NMR (100 MHz, DMSO-d$^6$) δ: 165.8, 149.3, 138.6, 132.2, 129.9, 128.3, 113.3, 104.9, 56.8, 2.0.

Example 2

Reduction of Cytotoxicity in an HD Striatal Cell Model

Reduction of Cytotoxicity by the A4 Inhibitor in an HD Striatal Cell Model: Results from previous experiments demonstrated that murine striatal cells (STHdh$^{Q7/7}$) were more sensitive to ER stress-inducing drugs than other cell types and expression of Htt111Q (STHdh$^{Q111/111}$ cells) further increased this stress sensitivity [Leitman et al., PLoS One 2014, 9(3):e90803]. As the activity of PERK was particularly affected in the Huntington's disease (HD) models [Leitman et al., PLoS One 2014, 9(3):e90803], the therapeutic capacity of a PERK inhibitor named A4 [Wang et al., Chem Biol Drug Des 2010, 76:480-495] was tested in cells expressing polyQ-expanded Htt, as depicted in Background art FIG. 1. The results are presented in FIGS. 2A-2D.

As shown in FIGS. 2A and 2B, A4 was able to diffuse through the cell membrane and specifically inhibit PERK (eIF2αK3) upon its induction by tunicamycin (FIG. 2A), and not inhibit cytosolic PKR (eIF2αK2), another kinase of eIF2α, upon its induction by poly-I.C (FIG. 2B).

As shown in FIG. 2C, the cytotoxicity in STHd$^{Q111/111}$ cells was specifically reduced by A4, which rescued the cells in a dose-dependent manner. In contrast, as shown in FIG. 2D, no effect was displayed by a PKR inhibitor on cytotoxicity in STHdh$^{Q111/111}$ cells. Each inhibitor was used at its normal inhibitory range.

Effect of the Novel PERK Inhibitors on the HD Cellular Model:

The activity of the novel inhibitors, compared to A4, in preventing cytotoxicity induced by pathogenic Htt, was then tested. A stable murine striatal cell line expressing full-length polyQ-expanded Htt, STHdh$^{Q111/111}$, was used. The results are presented in FIGS. 3A-3B.

Figure 3A:
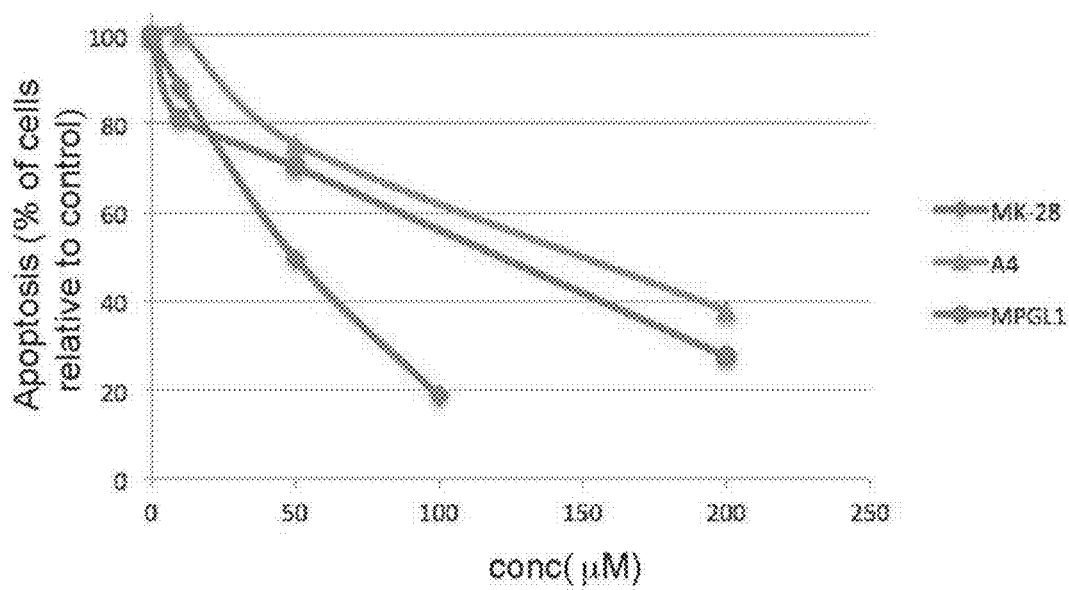
FIGS. 3A-3B present comparative plots showing the rescue of STHdhQ111/111 cells by exemplary PERK inhibitors according to the present embodiments.

As shown in FIG. 3A, MPGL1 (Compound 1) was more potent than A4 in inhibiting ER stress-induced cell death in cells expressing mutant Htt111Q upon exposure to tunicamycin, especially at the low concentration range. As further shown in FIG. 3A, Compound 3 (MK-28) was significantly more potent than A4 (>3 fold lower IC50 for inhibition of cytotoxicity in the STHdh$^{Q111/111}$ cells) in the presence of additional ER stress caused by tunicamycin.

Figure 3B:
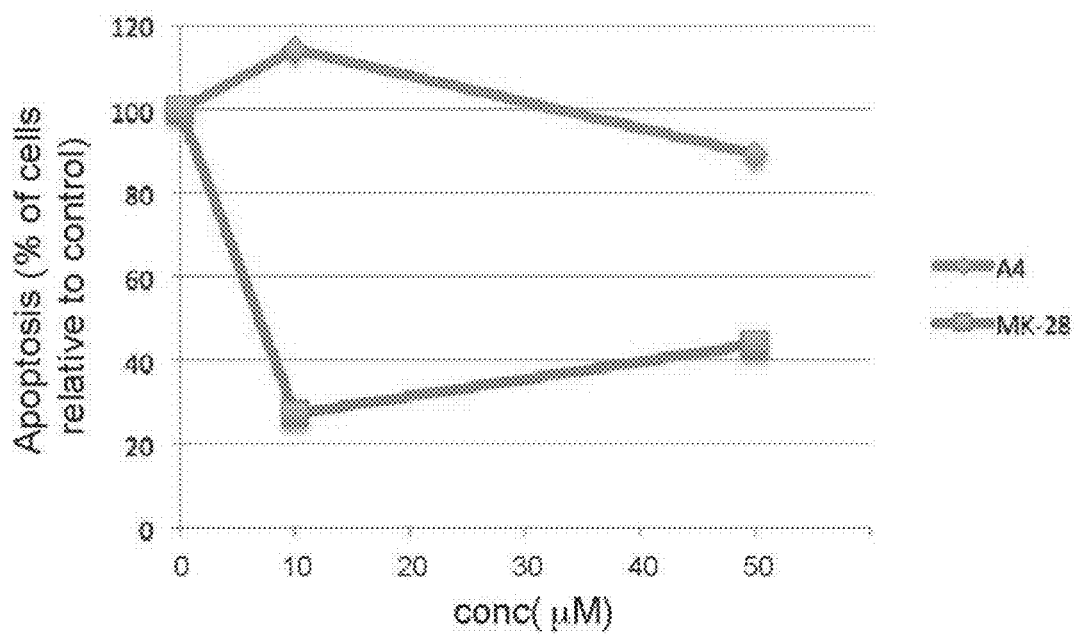

As shown in FIG. 3B, Compound 3 (MK-28) had a strong protective effect, in the low micromolar range, in cells incubated without serum without addition of an ER stressor; whereas A4 showed almost no protection under such conditions.

Furthermore, neither MPGL1 nor MK-28 exhibited intrinsic cytotoxicity on cells.

Toxicity:

MK-28 toxicity was tested in pancreatic beta cells, the type of cell that is most sensitive when ER stress response pathways are affected. A conditionally transformed mouse pancreatic islet beta-cell line (betaTC-tet), such as described by Efrat [Ann NY Acad Sci 1999, 875:286-293], was used. These cells produce high amounts of insulin, resulting in a high protein load in the ER, making them very sensitive to ER stress and other stimuli, such as cytokine effects. Compromising any of the UPR branches leads to cytotoxicity in these cells. MK-28 was compared to the ER stressor tunicamycin (Tun).

Figure 4:
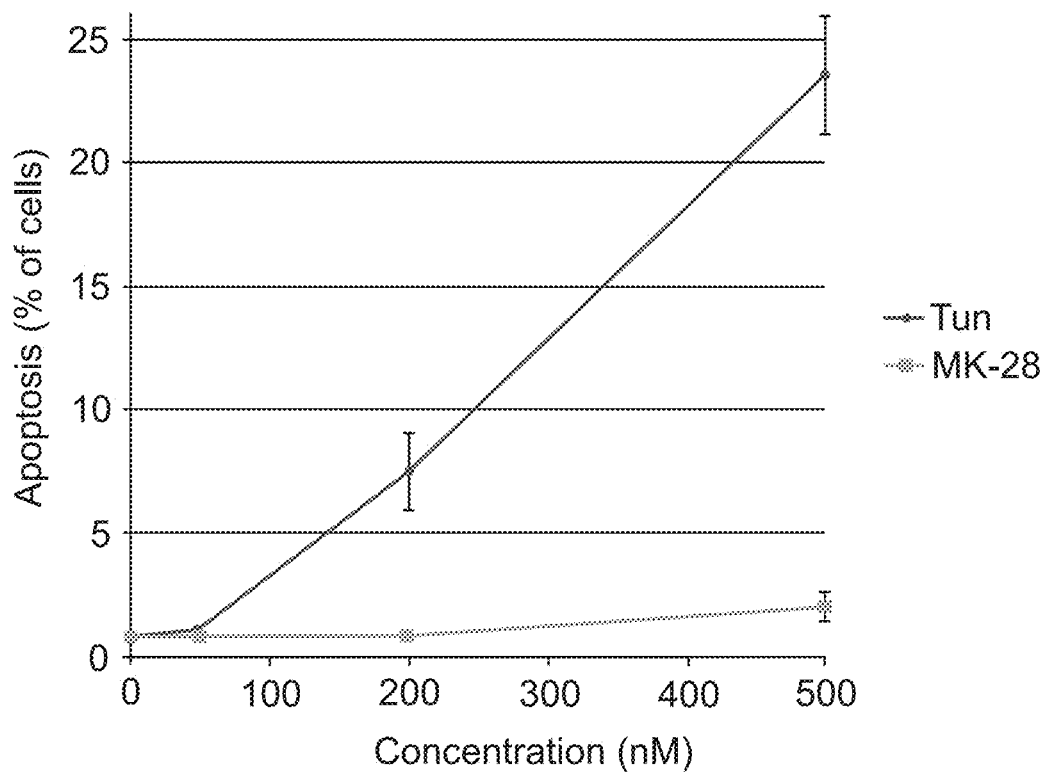
FIG. 4 presents a comparative analysis of toxicity in pancreatic beta cells. A conditionally transformed mouse pancreatic islet beta-cell line (betaTC-tet) was used. MK-28 was compared to the ER stressor tunicamycin (Tun). At the tested concentration range, MK-28 had very low toxicity, whereas Tun was toxic.

As shown in FIG. 4, MK-28 had very low toxicity throughout the tested concentration range (up to 500 nm), whereas Tun was toxic.

Example 3

HD Mouse Model

To test the therapeutic potential of the PERK inhibitors, an HD mouse model was used. Specifically, the R6/2 transgenic mice model was used. R6/2 mice express only exon 1 of the human Htt gene, including 150 CAG repeats driven by the human Htt promoter directly influencing the transgene expression levels and thereby the development of HD-like pathology [Mangiarini et al., Cell 1996, 87:493-506; Li et al., NeuroRx 2005, 2:447-464].

Toxicity:

MK-28 (Compound 3) toxicity was tested in wild type (WT) mice and no toxic effects were observed after administration of 6 mg/kg (6 times the dose used for the therapeutic experiment) for 2 weeks using continuous dosing with a subcutaneous implantation of an Alzet pump model 1002, with a rate of 0.11 μl/hour.

Pharmacokinetics (PK) and Blood Brain Barrier (BBB) Penetration:

Pharmacokinetics (PK) and blood brain barrier (BBB) penetration were analyzed in WT mice.

Figure 5:
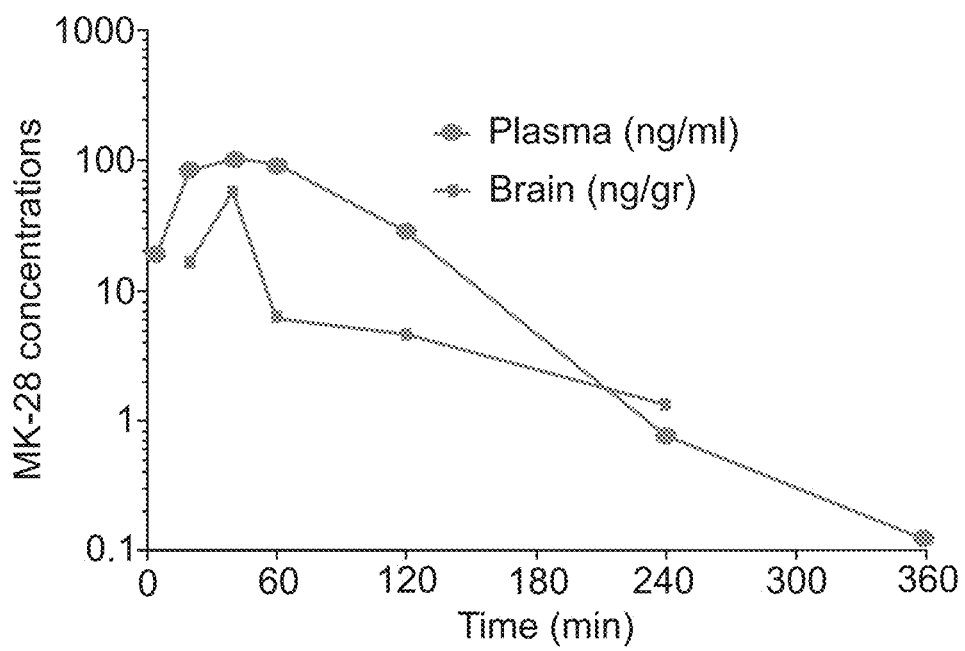
FIG. 5 Analysis of Pharmacokinetics (PK) and blood brain barrier (BBB) penetration was done in WT mice using a method based on LC/MS/MS. The results showed very good brain bioavailability of the compound, the peak of MK-28 concentration (105 ng/ml) was detected in plasma after 40 minutes, $T_{1/2}$=30 minutes, following 10 mg/kg MK-28 by IP injection. BBB penetration showed a peak of more than 50% of the concentration in plasma, (57 ng/ml) achieved after 40 minutes, $T_{1/2}$=80 minutes.

As shown in FIG. 5, the peak of MK-28 plasma concentration (105 ng/ml) was detected 40 minutes after administration of 10 mg/kg MK-28 by IP injection, with a $T_{1/2}$ value of 30 minutes. As further shown therein, BBB penetration showed a peak of more than 50% of the concentration in plasma (57 ng/ml) achieved 40 minutes after administration, with a $T_{1/2}$ value of 80 minutes (FIG. 5), indicating very good brain bioavailability of the compound.

Motor and Behavioral Tests:

For the therapeutic assessment of MK-28 delivery, Alzet pumps models 1004, with a rate of 0.11 μl/hour and 28 days compound delivery were used. Five groups of mice were studied: (1) Transgenic (TG) treated with MK-28, (2) TG without treatment (pumps with vehicle), (3) Wild-type (WT) treated with MK-28, (4) WT without treatment (pumps with vehicle), (5) WT without pumps.

Alzet pumps were implanted at 4 weeks of age and MK-28 was administered at 1 mg/kg with continuous dosing for 28 days. This concentration is in a typical clinical dose range. The mice's motor function and coordination were tested by Rotarod, and limb clasping, ledge, gait and kyphosis were also tested. Vocalization tests were also performed and survival was assessed. Tests were performed in two independent blind experiments.

Weight evaluation during 7 weeks after pump implantation showed no significant differences between animals that received MK-28 or vehicle, being TG or their WT littermates, supporting the lack of inherent toxicity associated with the MK-28 delivery (not shown).

Figure 6:
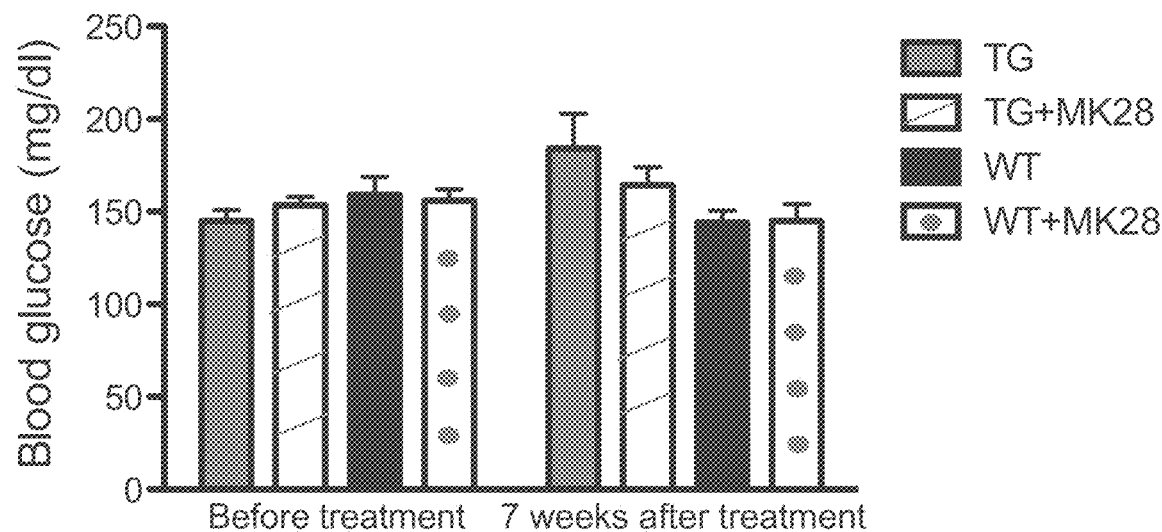
FIG. 6 is a bar graph demonstrating an increase in blood glucose levels in R6/2 mice and compensation thereof by MK-28 treatment. Animals were treated for 4 weeks starting at 4 weeks of age with 1 mg/ml MK-28 or with vehicle (DMSO/PEG400 1:1), delivered using Alzet pumps. TG mice (HD model R6/2 strain (Jackson laboratories stock #002810)) showed an increase in glucose levels, which was reduced with MK-28 treatment and remained low (7 weeks after start of treatment, 3 weeks after the end of administration of the compound). MK-28 did not affect glucose levels in the WT, suggesting no significant toxicity in the pancreas. N=13 TG, 13 TG+MK28, 16 WT, 15 WT+MK28, 15 None.

As shown in FIG. 6, blood glucose levels were increased in the TG mice and reduced by treatment with MK-28; whereas the compound had no effect on the glucose levels in the WT mice.

As in PERK knockout mice, pancreatic beta cells are affected and glucose levels altered, suggesting that at the administered levels, MK-28 inhibition is not so extreme as to affect pancreatic function.

Rotarod analysis was performed by assessing the maximum performance of each animal during three consecutive trials at different time points. The analysis evaluated the motor behavior of animals starting one week after the pump implantation (equivalent to the mice fifth week of life) and ending by seven weeks after first MK-28 delivery.

Data analysis showed no significant differences between the five groups during the first three weeks after the treatment initiation. However, eight weeks old mice (4 weeks after pump implantation) showed significant differences in performance between R6/2 TG mice and their control WT littermates.

Figure 7:
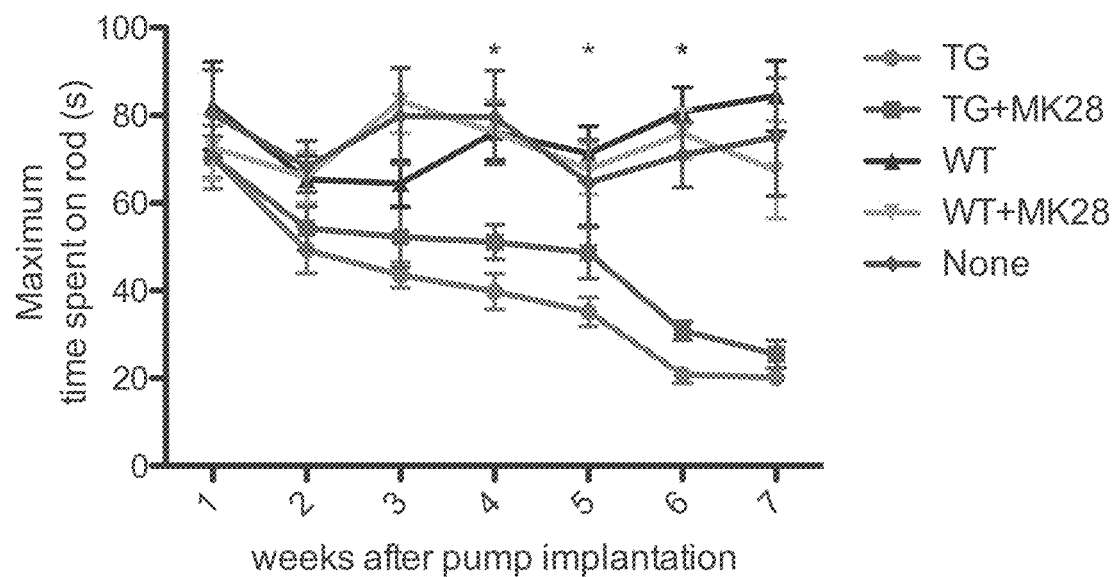
FIG. 7 presents comparative plots presenting data obtained in the Rotarod test and showing a significant improvement in motor function upon treatment of R6/2 mice with MK-28. TG mice showed a strong motor deficit, which was significantly reduced with MK-28 treatment, continuing after the end of administration of the compound. N=13 TG, 13 TG+MK28, 16 WT, 15 WT+MK28, 15 None. *p<0.05 Anova Newman-Keuls post hoc.

Moreover, as shown in FIG. 7, MK-28 treated TG mice showed significant improvement in general motor performance as compared to TG mice without treatment (p<0.05). This improvement was effectively sustained for three weeks after the end of MK-28 administration, until both TG groups met at week 7 after pump implantation, due to severe motor deficits associated with the R6/2 strain. WT mice without any intervention performed similarly to those that received pumps filled with vehicle or MK-28 compound, showing no significant differences between groups and no compromised motor performance associated with MK-28 treatment.

In parallel to the Rotarod analysis motor function and disease severity were evaluated using a simple composite phenotype that includes the combined analysis of hind limb clasping, ledge walk, gait and kyphosis [Guyenet et al., *J Vis Exp* 2010, (39):1787]. This test has the ability to effectively discriminate between affected and non-affected individuals, while also quantifying the temporal progression of neurodegenerative disease phenotypes such as HD.

As shown in FIG. 8, TG and WT mice performed differently starting from week four after pump implantation, in concordance with the results of the abovementioned rotarod test. From week 6 until the end of the analysis, TG mice treated with MK-28 showed lower scores than those without treatment, indicating a significant positive effect of the treatment on gait, clasping and general motor function (p<0.05). These results validate the model and test potency.

As further shown in FIG. 8, WT animals with or without pump or MK-28 performed similarly, again with no detrimental effect exerted by the tested compound in healthy animals (p>0.05), in agreement with results of the abovementioned rotarod test.

Vocalization was evaluated, as it reflects motor and cognitive abilities.

As shown in FIG. 9, while WT mice emit high number of syllables (230 in 5 minutes), the R6/2 mice produce few if any syllables (4.3 in 5 minutes). The MK-28-treated mice produced 13.75 syllables in 5 minutes. The effect of the MK-28 was very robust (three fold difference).

Survival:

As shown in FIG. 10, mice survival analysis showed a significant positive impact of MK-28 delivery in the lifespan of TG animals, considering that the drug was delivered only between age weeks 4 to 8. Median survival was increased by 8 days in treated TG mice (97 days) in comparison to their untreated counterparts (89 days). Moreover, death initiation in the TG MK-28 group was also delayed by almost 10 days when comparing them to animals treated with vehicle.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of alleviating a symptom of a disease or disorder associated with an aggregation-prone protein, the method comprising administering to a subject suffering from a symptom of said disease or disorder a therapeutically effective amount of a compound represented by Formula I:

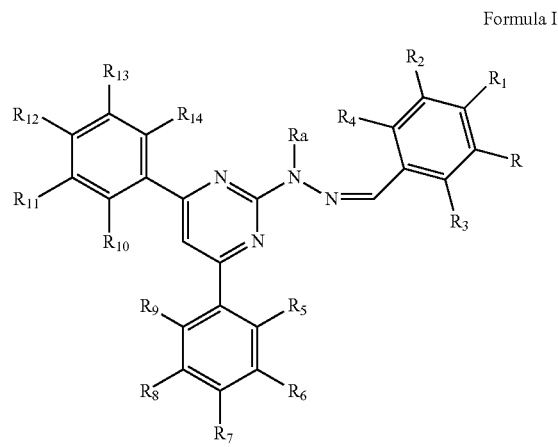

Formula I or a pharmaceutically acceptable salt thereof, wherein:

R is OH or OR';

$R_1$ and $R_2$ are each independently selected from the group consisting of hydrogen, OH and OR', wherein $R_1$ is OH and/or $R_2$ is OR';

R' is selected from the group consisting of alkyl, cycloalkyl, heteroalicyclic, aryl and heteroaryl;

Ra is hydrogen or alkyl; and $R_3$-$R_{14}$ are each independently selected from the group consisting of hydrogen, alkyl, alkenyl, alkynyl, cycloalkyl, aryl, heteroaryl, heteroalicyclic, halo, hydroxy, alkoxy, sulfonate, sulfoxide, thiosulfate, sulfate, sulfite, thiosulfite, phosphonate, thiohydroxy, thioalkoxy, cyano, nitro, azo, sulfonamide, carbonyl, thiocarbonyl, C-carboxylate, O-carboxylate, N-thiocarbamate, O-thiocarbamate, acyl halide, azide, urea, thiourea, N-carbamate, O-carbamate, C-amide, N-amide, hydrazine and hydrazide, with the proviso that when R is OR', and R' is methyl, $R_7$ and $R_{12}$ are each other than bromo, thereby alleviating the symptom of a disease or disorder associated with an aggregation-prone protein.

2. The method of claim 1, wherein said disease or disorder is selected from the group consisting of Huntington's disease, amyloidosis, cataract, type II diabetes, cancer and memory deficiency.

3. The method of claim 1, wherein $R_7$ and $R_{12}$ are each other than bromo.

4. The method of claim 1, wherein $R_7$ and $R_{12}$ are each hydrogen.

5. The method of claim 1, wherein $R_2$-$R_4$ are each hydrogen.

6. The method of claim 1, wherein $R_5$-$R_{14}$ are each hydrogen.

7. The method of claim 1, wherein $R_2$-$R_{14}$ are each hydrogen.

8. The method of claim 1, wherein $R_1$ is OH.

9. The method of claim 1, wherein Ra is methyl.

10. The method of claim 9, wherein R is OR'.

11. The method of claim 10, wherein R' is methyl.

12. The method of claim 9, wherein R is OH.

13. The method of claim 9, wherein the compound is selected from the group consisting of:

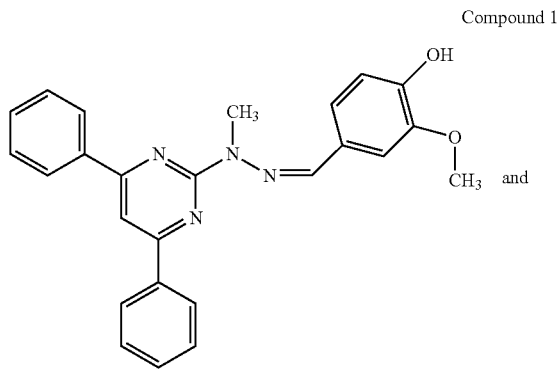

Compound 1 and

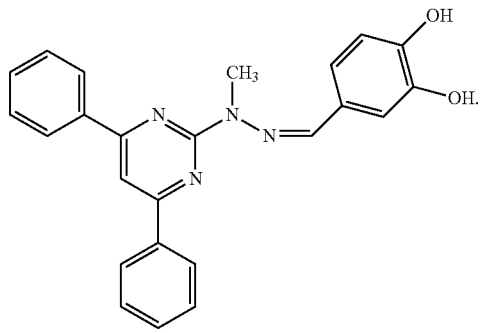

Compound 3

14. The method of claim 1, wherein Ra is hydrogen.

15. The method of claim 14, wherein $R_7$ and $R_{12}$ are each hydrogen.

16. The method of claim 14, wherein $R_5$-$R_{14}$ are each hydrogen.

17. The method of claim 14, wherein $R_2$-$R_{14}$ are each hydrogen.

18. The method of claim 14, wherein $R_1$ is OH.

19. The method of claim 14, wherein R is OH.

20. The method of claim 17, wherein R and $R_1$ are each OH.

* * * * *